(12) United States Patent
Skerra et al.

(10) Patent No.: US 11,034,938 B2
(45) Date of Patent: Jun. 15, 2021

(54) MICROORGANISM EXPRESSING MUTANT ALKB ENZYME AND USE TO PREPARE OMEGA-HYDROXY CARBOXYLIC ACID AND/OR ESTER

(71) Applicant: EVONIK DEGUSSA GMBH, Essen (DE)

(72) Inventors: Arne Skerra, Dachau (DE); Ludwig Kirmair, Erding (DE); Steffen Schaffer, Herten (DE); Christoph Schorsch, Frankfurt am Main (DE); Mirja Wessel, Bochum (DE); Thomas Haas, Münster (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 16/314,768

(22) PCT Filed: Jul. 3, 2017

(86) PCT No.: PCT/EP2017/066445
§ 371 (c)(1),
(2) Date: Jan. 2, 2019

(87) PCT Pub. No.: WO2018/007289
PCT Pub. Date: Jan. 11, 2018

(65) Prior Publication Data
US 2019/0153405 A1    May 23, 2019

(30) Foreign Application Priority Data
Jul. 4, 2016   (EP) ..................................... 16177711

(51) Int. Cl.
*C12N 9/02* (2006.01)
*C12P 7/64* (2006.01)
(52) U.S. Cl.
CPC .......... *C12N 9/0077* (2013.01); *C12P 7/6472* (2013.01); *C12Y 114/15003* (2013.01)
(58) Field of Classification Search
None
See application file for complete search history.

(56) References Cited

U.S. PATENT DOCUMENTS

| | | | | |
|---|---|---|---|---|
| 8,309,333 B1* | 11/2012 | Koch | ................... | C12N 9/0077 |
| | | | | 435/183 |
| 9,012,227 B2* | 4/2015 | Karau | ................... | C08G 69/08 |
| | | | | 435/471 |
| 10,053,713 B2* | 8/2018 | Pfeffer | ...................... | C12P 7/24 |
| 10,174,353 B2* | 1/2019 | Thum | ...................... | C12N 9/14 |
| 10,450,590 B2* | 10/2019 | Haas | ........................ | C12P 7/62 |
| 2010/0324257 A1* | 12/2010 | Karau | ................... | C08G 69/08 |
| | | | | 528/310 |
| 2013/0052700 A1 | 2/2013 | Poetter et al. | | |
| 2013/0143301 A1 | 6/2013 | Bott et al. | | |
| 2014/0141478 A1 | 5/2014 | Schaffer et al. | | |
| 2014/0178948 A1 | 6/2014 | Schaffer et al. | | |
| 2014/0256904 A1 | 9/2014 | Schaffer et al. | | |

FOREIGN PATENT DOCUMENTS

| | | |
|---|---|---|
| EP | 2607490 | 6/2013 |
| EP | 2730655 | 5/2014 |
| EP | 2746397 | 6/2014 |
| JP | 2013-511280 | 4/2013 |
| JP | 2014-121325 | 7/2014 |
| WO | 2011/131420 | 10/2011 |
| WO | 2013/024114 | 2/2013 |

OTHER PUBLICATIONS

Li et al. Biotechnol Bioeng. Jul. 2014;111 (7):1273-87. Epub May 6, 2014. (Year: 2014).*
Bornscheuer et al. Curr Protoc Protein Sci. Nov. 2011;Chapter 26:Unit26.7. (Year: 2011).*
Chica et al. CurrOpin Biotechnol. Aug. 2005;16(4):378-84. (Year: 2005).*
Singh et al. Curr Protein PeptSci. 2017, 18, 1-11 (Year: 2017).*
Alignment of SEQ ID No. 1 to SEQ ID No. 2 of U.S. Pat. No. 8,309,333. 2020 (Year: 2020).*
Kizer et al. Appl Environ Microbiol. May 2008;74(10):3229-41. (Year: 2008).*
Prather et al. CurrOpin Biotechnol. Oct. 2008;19(5):468-74. (Year: 2008).*
European Search Report for EP 16177711.5 dated Jan. 9, 2017 (10 pages).
Liu, C, et al. Isolation of an alkane-degrading *Alcanivorax* sp. Strain 2B5 and cloning of the alkB gene. Bioresource Technology. 2010. vol. 101. pp. 310-316.
Database UniProt [Online]. Feb. 17, 2016, "SubName: Full=Alkane 1-monooxygenase {EC0:0000313:EMBL:KPK57499.1};" XP002765213, (retrieved from EBI accession No. UNIPROT:AOAOS8FCR1. Database accession No. AOAOS8FCR1. 1 page.
Database UniProt [Online]. Jun. 16, 2009, "SubName: Full=Alkane hydroxylase {EC0:0000313:EMBL:ACQ44675.1};", XP002765214, retrieved from EBI accession No. UNIPROT:C3W4W7; Database accession No. C3W47, 1 Page.
Hermann, T. et al. Proteome analysis of Corynebacterium glutamicum. Electrophoresis. 2001. vol. 22. pp. 1712-1723.
Lohaus, C. et al. Proteomforschung. Biospektrum. 1989, vol. 5. pp. 32-36.

(Continued)

*Primary Examiner* — Christian L Fronda
(74) *Attorney, Agent, or Firm* — Smith, Gambrell & Russell, LLP

(57) ABSTRACT

There is provided a microbial cell expressing a mutant AlkB enzyme, the mutant AlkB enzyme comprising at least one point mutation in the wild type sequence of AlkB, wherein the point mutation is at amino acid position V129 and/or T136 of the wild type AlkB enzyme. There is also provided a method for producing omega-hydroxy carboxylic acid and/or ester thereof using this cell.

13 Claims, 1 Drawing Sheet
Specification includes a Sequence Listing.

(56) References Cited

OTHER PUBLICATIONS

Lottspeich, Friedrich. Proteomanalyse—ein Weg zur Funktionsanalyse von Proteinen. Angew. Chem. 1999. vol. 111. pp. 2630-2647.
International Preliminary Report on Patentability dated Jan. 8, 2019 for International Patent Application No. PCT/EP2017/066445 (8 pages).
International Search Report for PCT/EP2017/066445, dated Sep. 21, 2017 (3 pages).
Written Opinion for PCT/EP2017/066445, dated Sep. 21, 2017 (7 pages).
Office Action dated Mar. 2, 2021 for Japanese Patent Application No. 2018-567827 (5 pages in Japanese with English translation).

* cited by examiner

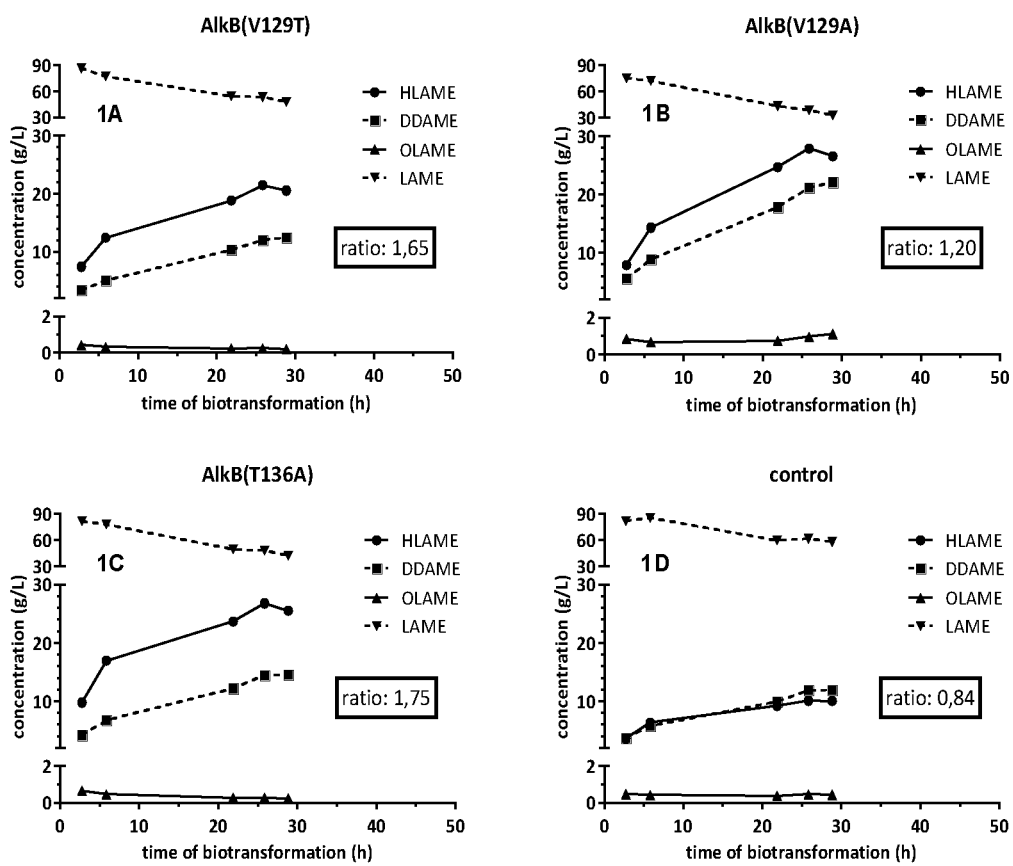

MICROORGANISM EXPRESSING MUTANT ALKB ENZYME AND USE TO PREPARE OMEGA-HYDROXY CARBOXYLIC ACID AND/OR ESTER

FIELD OF THE INVENTION

The present invention relates to a biotechnological means for producing at least one omega-hydroxy carboxylic acid and/or ester thereof from at least one $C_6$-$C_{14}$ carboxylic acid. In particular, the biotechnological means may use a mutant AlkB gene comprising at least one specific point mutation that may be capable of producing omega-hydroxy carboxylic acid and/or ester thereof specifically.

BACKGROUND OF THE INVENTION

Omega-hydroxylated (ω-hydroxy) carboxylic acid derivatives have many commercial uses as components of industrial agents. Some examples of ω-hydroxy carboxylic acid derivatives that are useful in the industrial world include ω-hydroxy carboxylic acids; ω-hydroxy carboxylic acid methyl esters; ω-oxo carboxylic acids; ω-amino carboxylic acids; ω-amino carboxylic acid methyl esters; alpha-, omega-diacids (α,ω-diacids); omega-carboxy carboxylic acid methyl esters (ω-carboxy carboxylic acid methyl ester); alpha-, omega-diesters (α,ω-diesters); alpha-, omega-diols (α,ω-dials); and the like. These compounds may be also be used as precursors for the production of other various compounds. For example, these precursors may be used for the production of α,ω-dicarboxylic acids, and α,ω-bifunctional molecules are especially important chemicals in industrial applications for polymer resins, metal working fluids, adhesives, corrosion inhibitors, capacitor electrolytes, diester synthetic lubricants, fibres, powder coating curatives, plasticizers, polyester coatings, epoxy resins, polyamide resins, flavours, fragrances, surfactants, detergents, additives, and the like.

Generally, ω-hydroxy carboxylic acid derivatives are mainly produced from petroleum-based materials or from bioconversion of paraffin and carboxylic acids to ω-hydroxy carboxylic acid and/or derivatives thereof. The chemical methods for producing these compounds require the use of hazardous reagents. The methods used in the art are also energy intensive and cause much damage to the environment. The alternative emerging fermentation routes, while considered green processes, are still too expensive and are limited in the types and amounts of products that can be made.

Accordingly, there is a need in the art for improved green methods of producing ω-hydroxy carboxylic acid and derivatives thereof.

In one example of producing omega-amino lauric methyl ester, the precursor may be lauric acid methyl ester (LAME) where the intermediate may be omega-hydroxylauric acid methylester (HLAME). The monooxygenase AlkB is an enzyme known to catalyse the reaction forming HLAME from LAME. The AlkB enzyme is also able to catalyse the oxidation of HLAME to omega-oxolauric acid methylester (OLAME). The monooxygenase AlkB is thus capable of catalysing both the oxidation steps resulting in the formation of OLAME from LAME via HLAME. However, AlkB enzyme is further capable of catalysing the conversion of OLAME to dodecanedioic acid monomethylester (DDAME), which results in the reduced product yield of OLAME.

There is thus a need in the art for an improved biotechnological method that increases the yield of specific omega-hydroxylated carboxylic acids and/or esters thereof from the corresponding carboxylic acids and/or esters thereof used as substrate with reduced production of unnecessary by-products. There is also a need in the art to increase the yield of the desired products such as HLAME and/or OLAME effectively.

DESCRIPTION OF THE INVENTION

The present invention attempts to solve the problems above by providing a mutant AlkB enzyme comprising at least one point mutation relative to the wild type enzyme. The mutant enzyme may be transcribed in at least one cell to produce a microbial cell expressing the mutant AlkB enzyme. This cell expressing the mutant AlkB enzyme may be capable of producing at least one omega-hydroxylated carboxylic acid and/or ester thereof from the corresponding carboxylic acid and/or ester thereof used as substrate. In particular, the carboxylic acid and/or ester thereof may be selected from the group consisting of $C_6$-$C_{14}$ carboxylic acids and/or esters thereof. In particular, this cell expressing the mutant AlkB enzyme may be capable of producing more omega-hydroxylated carboxylic acids and/or esters thereof relative to a cell expressing the wild type AlkB enzyme. The yield of omega-hydroxylated carboxylic acids and/or esters thereof from the cell expressing the mutant AlkB enzyme is greater relative to the cell expressing the wild type AlkB enzyme. In one example, the mutant AlkB may be capable of increased omega-hydroxylauric acid methyl ester (HLAME) production and/or accumulation in the cell where the mutant AlkB is expressed relative to a wild type cell (i.e. where the mutant AlkB enzyme is not expressed).

According to one aspect of the present invention, there is provided at least one microbial cell expressing a mutant AlkB enzyme, the mutant AlkB enzyme comprising at least one point mutation in the wild type sequence of AlkB, wherein the point mutation is at amino acid position V129 and/or T136 of the wild type AlkB enzyme. In particular, the point mutation in the mutant AlkB enzyme is at amino acid position V129 and/or T136 of the wild type AlkB enzyme.

The archetype of this class of oxidoreductases, AlkB, is a redox protein from the *Pseudomonas putida* AlkBGT system, dependent on two auxiliary polypeptides, AlkG and AlkT. AlkT is a FAD-dependent rubredoxin reductase transferring electrons from NADH to AlkG. AlkG is a rubredoxin, an iron-containing redox protein functioning as a direct electron donor to AlkB. In an example, the term "AlkB-type oxidoreductases", as used herein, refers to a rubredoxin-dependent oxidoreductase having a hydrocarbon binding site. In particular, the term "hydrocarbon binding site", as used herein, refers to a stretch of the protein surface capable of binding to a hydrocarbon, particularly an alkane and/or alkene, more particularly within reach of the catalytic centre of the protein. In one example, the term "rubredoxin-dependent alkane oxidase", as used herein refers to an oxidoreductase that recognises as its substrate an alkane receiving electrons via a rubredoxin, the latter having, in a particular example, an iron-sulphur protein having an α+β class fold with 2 α helices and 2 to 3 β-strands transferring electrons to the alkane oxidase. More in particular, the alkB-type oxidoreductase may be AlkB from *Pseudomonas putida* Gpo1 (Access code: CAB54050.1, any access code used in the application refers to the respective sequence from the Genbank database run by the NCBI, wherein the release referred to is the one available online on the 15 Jan. 2012) or a variant thereof.

In particular, the wild type AlkB may comprise a polypeptide with sequence identity of at least 50, 60, 65, 70, 75, 80, 85, 90, 91, 94, 95, 98 or 100% to a polypeptide SEQ ID NO: 1. More in particular, the wild type AlkB has a polypeptide sequence that comprises the amino acids of SEQ ID NO:1 that are essential for the function, for example the catalytic activity of a protein, or the fold or structure of the protein. The other amino acids may be deleted, substituted or replaced by insertions or essential amino acids are replaced in a conservative manner to the effect that the biological activity of the wild type AlkB is preserved. In particular, the wild type AlkB according to any aspect of the present invention may comprise 70% sequence identity to SEQ ID NO: 1 wherein the wild type AlkB enzyme does not comprise a mutation at amino acid positions 129, 132 and 136. In particular, the wild type AlkB enzyme comprises amino acid valine (V) at amino acid position 129, leucine (L) at amino acid position 132 and threonine (T) at amino acid position 136.

The term "enzyme" means any substance composed wholly or largely of protein or polypeptides that catalyzes or promotes, more or less specifically, one or more chemical or biochemical reactions. An example of an enzyme used according to any aspect of the present invention may be AlkB. In particular, AlkB alkane hydroxylase or an alkane monooxygenase of EC 1.14.15.3. The AlkB alkane hydroxylase is a component of a reaction system comprising three enzyme components AlkB alkane hydroxylase of EC 1.14.15.3, AlkT rubredoxin NAD(P)+ reductase of EC 1.18.1.1 or of EC 1.18.1.4 and rubredoxin AlkG. AlkT is a FAD-dependent rubredoxin reductase transferring electrons from NADH to AlkG. AlkG is a rubredoxin, an iron-containing redox protein functioning as a direct electron donor to AlkB. In a preferred embodiment, the term "AlkB-type oxidoreductases", as used herein, refers to a rubredoxin-dependent oxidoreductase having a hydrocarbon binding site. The AlkB enzyme may comprise sequence identity of at least 50% to the alkane monooxygenase from *Pseudomonas putida* GPo1 encoded by AlkBGT. In particular, the AlkB wild type enzyme may comprise sequence identity of at least 70% to the polypeptide CAB54050.1 (SEQ ID NO:1; any access code used in the application refers to the respective sequence from the Genbank database run by the NCBI, wherein the release referred to is the one available online on the 28 Apr. 2016).

A "polypeptide" (one or more peptides) is a chain of chemical building blocks called amino acids that are linked together by chemical bonds called peptide bonds. A protein or polypeptide, including an enzyme, may be "native" or "wild-type", meaning that it occurs in nature or has the amino acid sequence of a native protein, respectively. These terms are sometimes used interchangeably. A polypeptide may or may not be glycosylated. The term "wild type" as used herein in conjunction with a cell or microorganism may denote a cell with a genome make-up that is in a form as seen naturally in the wild. The term may be applicable for both the whole cell and for individual genes. The term 'wild type' may thus also include cells which have been genetically modified in other aspects (i.e. with regard to one or more genes) but not in relation to the genes of interest. The term "wild type" therefore does not include such cells where the gene sequences of the specific genes of interest have been altered at least partially by man using recombinant methods. A wild type cell according to any aspect of the present invention thus refers to a cell that has no genetic mutation with respect to the whole genome and/or a particular gene. Therefore, in one example, a wild type AlkB may be an enzyme that is found naturally in nature without any of the specific mutations according to any aspect of the present invention. In another example, the wild type cell relative to the mutant AlkB according to any aspect of the present invention relates to a cell that has the natural/non-altered expression of AlkB with mutations that may occur naturally but not at amino acid positions 129, 132 and 136.

A polypeptide may also be a "mutant" meaning that it has been made, altered, derived, or is in some way different or changed from its wild-type form, or from another mutant. Mutant proteins typically have amino acid substitutions at one or more positions. Mutant DNA molecules typically have nucleotide substitutions in one or more positions. Mutant forms of a protein or DNA molecule can have the same, or altered, functions in comparison to the wild-type. For simplification, mutants may be referred to by their variation from the single amino acid code from which the mutation arose. For example, in one format the mutant is referred to as XPOSY, where "X" refers to the single letter code of the amino acid in the original sequence, "POS" refers to the position of the mutation in the sequence, and Y refers to the single letter code for the new amino acid appearing at the mutation's position. For example, V129T would mean that in the original protein, the amino acid at position 129 is a valine ("V"), but in the mutant, the valine is replaced with a threonine ("T").

In particular, the mutant AlkB enzyme according to any aspect of the present invention may comprise at least one point mutation at amino acid positions 129, 132 and/or 136 of the AlkB enzyme. In particular, the point mutations may be at amino acid positions 129, 132 or 136. In another example, the point mutation may be at amino acid position 129 and 132 or 129 and 136 or 132 and 136. In a further example, the point mutation may be at amino acid positions 129, 136 and 136. More in particular, the amino acid valine at position 129 may be converted to an amino acid selected from the group consisting of glycine, alanine, leucine, isoleucine, proline, phenylalanine, tyrosine, tryptophan, serine, threonine, cysteine, methionine, asparagine, glutamine, lysine, arginine, histidine, aspartate and glutamate. In particular, the amino acid valine at position 129 may be converted to an amino acid selected from the group consisting of threonine, alanine, serine, cysteine, asparagine and glycine. More in particular, the amino acid valine at position 129 may be converted to threonine or alanine. The amino acid threonine at position 136 may also be converted to an amino acid selected from the group consisting of glycine, alanine, leucine, isoleucine, proline, phenylalanine, tyrosine, tryptophan, serine, valine, cysteine, methionine, asparagine, glutamine, lysine, arginine, histidine, aspartate and glutamate. In particular, the amino acid threonine at position 136 may be converted to an amino acid selected from the group consisting of glycine, alanine, leucine, isoleucine, proline, phenylalanine, tryptophan, serine, valine, cysteine and methionine. The point mutations according to any aspect of the present invention may be position 129 and/or 136. In one example, the point mutation in mutant AlkB according to any aspect of the present invention may be at position 129. In another example, the point mutation in mutant AlkB according to any aspect of the present invention may be at position 136. In a further example, the point mutation in mutant AlkB according to any aspect of the present invention may be at position 129 and 136 in combination. More in particular, the point mutations of the cell according to any aspect of the present invention may be selected from the group consisting of V129T, T136A, V129A and combinations thereof relative to the wild type sequence of AlkB. The mutant AlkB enzyme may comprise V129T, T136A or V129A point mutation. In particular, the AlkB enzyme according to any aspect of the present invention may comprise the point mutation V129T. In one example, the AlkB enzyme may further comprise the point mutation T136A. In another example, the mutant AlkB enzyme of any cell according to any aspect of the present invention may comprise the point mutations V129T and T136A, V129A and T136A.

In particular, a microbial cell expressing a mutant AlkB enzyme, the mutant AlkB enzyme comprising at least one point mutation in the wild type sequence of AlkB, wherein the point mutation is at amino acid position V129 and/or T136 of the wild type AlkB enzyme wherein the point mutation at amino acid V129 is selected from the group consisting of V129T and V129A. More in particular, the point mutation may be at amino acid position T136. Even more in particular, the point mutation at amino acid position T136 may be T136A. In one example, when the point mutation is at amino acid position V129, the mutation may be selected from the group consisting of V129T and V129A. In another example, the point mutation may be at amino acid positions V129 and T136. In particular. the point mutation at amino acid position V129 may be selected from the group consisting of V129T and V129A and the point mutation at amino acid position T136 is T136A.

In particular, the point mutation may be V129A. In one example, the wild type sequence may be SEQ ID NO:1 or a variant thereof.

A "variant" of AlkB or at least SEQ ID NO:1, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "non-conservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software. According to any aspect of the present invention, the variant of SEQ ID NO:1 used as the wild type AlkB may not comprise a mutation at amino acid positions 129, 132 and/or 136.

Any techniques in molecular biology can be used for producing AlkB enzymes with specific point mutations. The term 'point mutation', or single base modification, is a type of mutation that causes a single nucleotide base change, insertion, or deletion of the genetic material, DNA or RNA. In one example, point mutation may refer to an amino acid substitution in a wild type sequence of AlkB gene. Some examples of method that may be used include error-prone polymerase chain reaction, cassette mutagenesis (in which the specific region optimized is replaced with a synthetically mutagenized oligonucleotide), oligonucleotide-directed mutagenesis, parallel PCR (which uses a large number of different PCR reactions that occur in parallel in the same vessel, such that the product of one reaction primes the product of another reaction), random mutagenesis (e.g., by random fragmentation and reassembly of the fragments by mutual priming); site-specific mutations (introduced into long sequences by random fragmentation of the template followed by reassembly of the fragments in the presence of mutagenic oligonucleotides); parallel PCR (e.g., recombination on a pool of DNA sequences); sexual PCR; and chemical mutagenesis (e.g., by sodium bisulfite, nitrous acid, hydroxylamine, hydrazine, formic acid, or by adding nitrosoguanidine, 5-bromouracil, 2-aminopurine, and acridine to the PCR reaction in place of the nucleotide precursor; or by adding intercalating agents such as proflavine, acriflavine, quinacrine); irradiation (X-rays or ultraviolet light, and/or subjecting the polynucleotide to propagation in a host cell that is deficient in normal DNA damage repair function); or DNA shuffling (e.g., in vitro or in vivo homologous recombination of pools of nucleic acid fragments or polynucleotides). Any one of these techniques can also be employed under low-fidelity polymerization conditions to introduce a low level of point mutations randomly over a long sequence, or to mutagenize a mixture of fragments of unknown sequence.

Any of the enzymes used according to any aspect of the present invention, may be an isolated enzyme. In particular, the enzymes used according to any aspect of the present invention may be used in an active state and in the presence of all cofactors, substrates, auxiliary and/or activating polypeptides or factors essential for its activity. The term "isolated", as used herein, means that the enzyme of interest is enriched compared to the cell in which it occurs naturally. The enzyme may be enriched by SDS polyacrylamide electrophoresis and/or activity assays. For example, the enzyme of interest may constitute more than 5, 10, 20, 50, 75, 80, 85, 90, 95 or 99 percent of all the polypeptides present in the preparation as judged by visual inspection of a polyacrylamide gel following staining with Coomassie blue dye.

According to any aspect of the present invention, the microbial cell may be selected from the species of bacteria from the group consisting of, *Abiotrophia, Acaryochloris, Accumulibacter, Acetivibrio, Acetobacter, Acetohalobium, Acetonema, Achromobacter, Acidaminococcus, Acidimicrobium, Acidiphilium, Acidithiobacillus, Acidobacterium, Acidothermus, Acidovorax, Acinetobacter, Actinobacillus, Actinomyces, Actinosynnema, Aerococcus, Aeromicrobium, Aeromonas, Afipia, Aggregatibacter, Agrobacterium, Ahrensia, Akkermansia, Alcanivorax, Alicycliphilus, Alicyclobacillus, Aliivibrio, Alkalilimnicola, Alkaliphilus, Allochromatium, Alteromonadales, Alteromonas, Aminobacterium, Aminomonas, Ammonifex, Amycolatopsis, Amycolicicoccus, Anabaena, Anaerobaculum, Anaerococcus, Anaerofustis, Anaerolinea, Anaeromyxobacter, Anaerostipes, Anaerotruncus, Anaplasma, Anoxybacillus, Aquifex, Arcanobacterium, Arcobacter, Aromatoleum, Arthrobacter, Arthrospira, Asticcacaulis, Atopobium, Aurantimonas, Azoarcus, Azorhizobium, Azospirillum, Azotobacter, Bacillus, Bartonella, Basfia, Baumannia, Bdellovibrio, Beggiatoa, Beijerinckia, Bermanella, Beutenbergia, Bifidobacterium, Bilophila, Blastopirellula, Blautia, Blochmannia, Bordetella, Borrelia, Brachybacterium, Brachyspira, Bradyrhizobium, Brevibacillus, Brevibacterium, Brevundimonas, Brucella, Buchnera, Bulleidia, Burkholderia, Butyrivibrio, Caldalkalibacillus, Caldanaerobacter, Caldicellulosiruptor, Calditerrivibrio, Caminibacter, Campylobacter, Carboxydibrachium, Carboxydothermus, Cardiobacterium, Carnobacterium, Carsonella, Catenibacterium, Catenulispora, Catonella, Caulobacter, Cellulomonas, Cellvibrio, Centipeda, Chelativorans, Chloroflexus, Chromobacterium, Chromohalobacter, Chthoniobacter, Citreicella, Citrobacter, Citromicrobium, Clavibacter, Cloacamonas, Clostridium, Collinsella, Colwellia, Comamonas, Conexibacter, Congregibacter, Coprobacillus,*

Coprococcus, Coprothermobacter, Coraliomargarita, Coriobacterium, corrodens, Corynebacterium, Coxiella, Crocosphaera, Cronobacter, Cryptobacterium, Cupriavidus, Cyanobium, Cyanothece, Cylindrospermopsis, Dechloromonas, Deferribacter, Dehalococcoides, Dehalogenimonas, Deinococcus, Delftia, Denitrovibrio, Dermacoccus, Desmospora, Desulfarculus, Desulphateibacillum, Desulfitobacterium, Desulfobacca, Desulfobacterium, Desulfobulbus, Desulfococcus, Desulfohalobium, Desulfomicrobium, Desulfonatronospira, Desulforudis, Desulfotalea, Desulfotomaculum, Desulfovibrio, Desulfurispirillum, Desulfurobacterium, Desulfuromonas, Dethiobacter, Dethiosulfovibrio, Dialister, Dichelobacter, Dickeya, Dictyoglomus, Dietzia, Dinoroseobacter, Dorea, Edwardsiella, Ehrlichia, Eikenella, Elusimicrobium, Endoriftia, Enhydrobacter, Enterobacter, Enterococcus, Epulopiscium, Erwinia, Erysipelothrix, Erythrobacter, Escherichia, Ethanoligenens, Eubacterium, Eubacterium, Exiguobacterium, Faecalibacterium, Ferrimonas, Fervidobacterium, Fibrobacter, Finegoldia, Flexistipes, Francisella, Frankia, Fructobacillus, Fulvimarina, Fusobacterium, Gallibacterium, Gallionella, Gardnerella, Gemella, Gemmata, Gemmatimonas, Geobacillus, Geobacter, Geodermatophilus, Glaciecola, Gloeobacter, Glossina, Gluconacetobacter, Gordonia, Granulibacter, Granulicatella, Grimontia, Haemophilus, Hahella, Halanaerobiumns, Haliangium, Halomonas, Halorhodospira, Halothermothrix, Halothiobacillus, Hamiltonella, Helicobacter, Heliobacterium, Herbaspirillum, Herminiimonas, Herpetosiphon, Hippea, Hirschia, Histophilus, Hodgkinia, Hoeflea, Holdemania, Hydrogenivirga, Hydrogenobaculum, Hylemonella, Hyphomicrobium, Hyphomonas, Idiomarina, Ilyobacter, Intrasporangium, Isoptericola, Isosphaera, Janibacter, Janthinobacterium, Jonesia, Jonquetella, Kangiella, Ketogulonicigenium, Kineococcus, Kingella, Klebsiella, Kocuria, Koribacter, Kosmotoga, Kribbella, Ktedonobacter, Kytococcus, Labrenzia, Lactobacillus, Lactococcus, Laribacter, Lautropia, Lawsonia, Legionella, Leifsonia, Lentisphaera, Lepto/yngbya, Leptospira, Leptothrix, Leptotrichia, Leuconostoc, Liberibacter, Limnobacter, Listeria, Loktanella, Lutiella, Lyngbya, Lysinibacillus, Macrococcus, Magnetococcus, Magnetospirillum, Mahella, Mannheimia, Maricaulis, Marinithermus, Marinobacter, Marinomonas, Mariprofundus, Maritimibacter, Marvinbryantia, Megasphaera, Meiothermus, Melissococcus, Mesorhizobium, Methy/acidiphilum, Methylibium, Methylobacillus, Methy/obacter, Methy/obacterium, Methy/ococcus, Methy/ocystis, Methy/omicrobium, Methy/ophaga, Methy/ophila/es, Methy/osinus, Methyloversatilis, Methy/ovorus, Microbacterium, Micrococcus, Microco/eus, Microcystis, Microlunatus, Micromonospora, Mitsuokella, Mobiluncus, Moorella, Moraxella, Moritalla, Mycobacterium, Myxococcus, Nakamuralla, Natranaerobius, Neisseria, Neorickettsia, Neptuniibacter, Nitratifractor, Nitratiruptor, Nitrobacter, Nitrococcus, Nitrosomonas, Nitrosospira, Nitrospira, Nocardia, Nocardioides, Nocardiopsis, Nodularia, Nostoc, Novosphingobium, Oceanibulbus, Oceanicaulis, Oceanicola, Oceanithermus, Oceanobacillus, Ochrobactrum, Octadecabacter, Odysella, Oligotropha, Olsenella, Opitutus, Oribacterium, Orientia, Omithinibacillus, Oscillatoria, Oscillochloris, Oxalobacter, Paenibacillus, Pantoea, Paracoccus, Parascardovia, Parasutterella, Parvibaculum, Parvimonas, Parvularcula, Pasteurella, Pasteuria, Pectobacterium, Pediococcus, Pedosphaera, Pelagibaca, Pelagibacter, Pelobacter, Pelotomaculum, Peptoniphilus, Peptostreptococcus, Persephonella, Petrotoga, Phaeobacter, Phascolarctobacterium, Phenylobacterium, Photobacterium, Pirellula, Planctomyces, Planococcus, Plesiocystis, Polaromonas, Polaromonas, Polymorphum, Polynucleobacter, Poribacteria, Prochlorococcus, Propionibacterium, Proteus, Providencia, Pseudoalteromonas, Pseudo flavonifractor, Pseudomonas, Pseudonocardia, Pseudoramibacter, Pseudovibrio, Pseudoxanthomonas, Psychrobacter, Psychromonas, Puniceispirillum, Pusillimonas, Pyramidobacter, Rahnella, Ralstonia, Raphidiopsis, Regiella, Reinekea, Renibacterium, Rhizobium, Rhodobacter, Rhodococcus, Rhodoferax, Rhodomicrobium, Rhodopirellula, Rhodopseudomonas, Rhodospirillum, Rickettsia, Rickettsialla, Riesia, Roseburia, Roseibium, Roseiflexus, Roseobacter, Roseomonas, Roseovarius, Rothia, Rubrivivax, Rubrobacter, Ruegeria, Ruminococcus, Ruthia, Saccharomonospora, Saccharophagus, Saccharopolyspora, Sagittula, Salinispora, Salmonella, Sanguibacte, Scardovia, Sebaldella, Segniliparus, Selenomonas, Serratia, Shewanella, Shigella, Shuttleworthia, Sideroxydans, Silicibacter, Simonsiella, Sinorhizobium, Slackia, Sodalis, Solibacter, Solobacterium, Sorangium, Sphaerobacter, Sphingobium, Sphingomonas, Sphingopyxis, Spirochaeta, Sporosarcina, Stackebrandtia, Staphylococcus, Starkeya, Stenotrophomonas, Stigmatalla, Streptobacillus, Streptococcus, Streptomyces, Streptosporangium, Subdoligranulum, subvibrioides, Succinatimonas, Sulfitobacter, Sulfobacillus, Sulfuricurvum, Sulfurihydrogenibium, Sulfurimonas, Sulfurospirillum, Sulfurovum, Sutterella, Symbiobacterium, Synechocystis, Syntrophobacter, Syntrophobotulus, Syntrophomonas, Syntrophothermus, Syntrophus, taiwanensis, Taylorella, Teredinibacter, Terriglobus, Tha/assiobium, Thauera, Thermaerobacter, Thermanaerovibrio, Thermincola, Thermoanaerobacter, Thermoanaerobacterium, Thermobaculum, Thermobifida, Thermobispora, Thermocrinis, Thermodesulphateator, Thermodesulfobacterium, Thermodesulfobium, Thermodesulfovibrio, Thermomicrobium, Thermomonospora, Thermosediminibacter, Thermosinus, Thermosipho, Thermosynechococcus, Thermotoga, Thermovibrio, Thermus, Thioalkalimicrobium, Thioalkalivibrio, Thiobacillus, Thiomicrospira, Thiomonas, Tolumonas, Treponema, tribocorum, Trichodesmium, Tropheryma, Truepera, Tsukamurella, Turicibacter, Variovorax, Veillonella, Verminephrobacter, Verrucomicrobium, Verrucosispora, Vesicomyosocius, Vibrio, Vibrionales, Victivallis, Weissella, Wigglesworthia, Wolbachia, Wolinella, Xanthobacter, Xanthomonas, Xenorhabdus, Xylanimonas, Xylella, Yersinia, Zinderia and Zymomonas, In particular, the microbial cell may be from *E. coli*, *Pseudomonas* sp., *Pseudomonas fluorescens*, *Pseudomonas putida*, *Pseudomonas stutzeri*, *Acinetobacter* sp., *Burkholderia* sp., *Burkholderia thailandensis*, *Cyanobakterien*, *Klebsiella* sp., *Klebsiella oxytoca*, *Salmonella* sp., *Rhizobium* sp. and *Rhizobium meliloti*, *Bacillus* sp., *Bacillus subtilis*, *Clostridium* sp., *Corynebacterium* sp., *Corynebacterium glutamicum*, *Brevibacterium* sp., *Chlorella* sp. and *Nostoc* sp. More in particular, the microbial cell may be *E. coli*.

In another example, the microbial cell may be a yeast cell. Suitable yeasts according to any aspect of the present invention may belong to the genera listed at http://www.dsmz.de/species/yeasts.htm. In particular, the yeast may be selected from the group consisting of *Schizosaccharomyces pombe*, *Schizosaccharomyces cerevisiae* and *Pichia pastoris*.

The enzyme used according to any aspect of the present invention may be recombinant. The term "recombinant" as used herein, refers to a molecule or is encoded by such a molecule, particularly a polypeptide or nucleic acid that, as such, does not occur naturally but is the result of genetic engineering or refers to a cell that comprises a recombinant molecule. For example, a nucleic acid molecule is recombinant if it comprises a promoter functionally linked to a sequence encoding a catalytically active polypeptide and the promoter has been engineered such that the catalytically active polypeptide is overexpressed relative to the level of the polypeptide in the corresponding wild type cell that comprises the original unaltered nucleic acid molecule.

A skilled person would be able to use any method known in the art to genetically modify a cell or microorganism. According to any aspect of the present invention, the genetically modified cell may be genetically modified so that in a defined time interval, within 2 hours, in particular within 8 hours or 24 hours, it forms at least once or twice, especially at least 10 times, at least 100 times, at least 1000 times or at least 10000 times more ω-functionalized carboxylic acid ester than the wild-type cell. The increase in product formation can be determined for example by cultivating the cell according to any aspect of the present invention and the wild-type cell each separately under the same conditions (same cell density, same nutrient medium, same culture conditions) for a specified time interval in a suitable nutrient medium and then determining the amount of target product (ω-functionalized carboxylic acid ester) in the nutrient medium. The genetically modified cell or microorganism may be genetically different from the wild type cell or microorganism. The genetic difference between the genetically modified microorganism according to any aspect of the present invention and the wild type microorganism may be in the presence of a complete gene, amino acid, nucleotide etc. in the genetically modified microorganism that may be absent in the wild type microorganism. In one example, the genetically modified microorganism according to any aspect of the present invention may comprise enzymes, in particular mutant AlkB that enables the microorganism to produce more HLAME relative to the wild type cell with the wild type or no AlkB expression. The wild type microorganism relative to the genetically modified microorganism of the present invention may have none or no detectable activity of the enzymes. As used herein, the term 'genetically modified microorganism' may be used interchangeably with the term 'genetically modified cell'. The genetic modification according to any aspect of the present invention is carried out on the cell of the microorganism.

The cells according to any aspect of the present invention are genetically transformed according to any method known in the art. In particular, the cells may be produced according to the method disclosed in WO2013024114. The phrase 'the genetically modified cell has an increased activity, in comparison with its wild type, in enzymes' as used herein refers to the activity of the respective enzyme that is increased by a factor of at least 2, in particular of at least 10, more in particular of at least 100, yet more in particular of at least 1000 and even more in particular of at least 10000.

The mutant AlkB enzyme according to any aspect of the present invention may be capable of
(a) catalysing the conversion of $C_6$-$C_{14}$ carboxylic acids and/or esters thereof as substrate to the corresponding omega-hydroxy carboxylic acid and/or esters thereof; or
(b) catalysing the conversion of $C_6$-$C_{14}$ carboxylic acids and/or esters thereof as substrate to the corresponding omega-oxocarboxylic acids and/or esters thereof.

The term "substrate" means any substance or compound that is converted or meant to be converted into another compound by the action of an enzyme catalyst. The term includes aromatic and aliphatic compounds, and includes not only a single compound, but also combinations of compounds, such as solutions, mixtures and other materials which contain at least one substrate. According to any aspect of the present invention, the substrate may be at least one $C_6$-$C_{14}$ carboxylic acid and/or esters thereof. The substrate may thus be selected from the group consisting of $C_6$, $C_7$, $C_8$, $C_9$, $C_{10}$, $C_{11}$, $C_{12}$, $C_{13}$, $C_{14}$ and esters thereof. The substrate may be a combination of $C_6$-$C_{14}$ carboxylic acid and/or esters thereof. In particular, the substrate may be at least one $C_8$-$C_{12}$ carboxylic acid and/or ester thereof, at least one $C_6$-$C_{10}$ carboxylic acid and/or ester thereof, or at least one $C_8$-$C_{10}$ carboxylic acid and/or ester thereof. In one example, the substrate may be lauric acid and/or ester thereof. In particular, the ester may be an ethyl or methyl ester of the carboxylic acid. In one example, the ester as substrate according to any aspect of the present invention may be methyl lauric acid methyl ester (LAME). In this example, the mutant AlkB may be capable of catalysing the oxidation reaction of conversion of lauric acid and/or lauric acid methyl ester (LAME) to omega-hydroxy lauric acid and/or omega-hydroxylauric acid methyl ester (HLAME) respectively. In another example, the mutant AlkB may be capable of catalysing the conversion of lauric acid and/or lauric acid methyl ester (LAME) to omega-oxo lauric acid and/or omega-oxolauric acid methyl ester (OLAME) respectively. In yet a further example, the mutant AlkB may be capable of catalysing the conversion of lauric acid and/or lauric acid methyl ester (LAME) to omega-hydroxy lauric acid and/or omega-hydroxylauric acid methyl ester (HLAME) and omega-oxo lauric acid and/or omega-oxolauric acid methyl ester (OLAME) concurrently.

An "oxidation reaction" or "oxygenation reaction", as used herein, is a chemical or biochemical reaction involving the addition of oxygen to a substrate, to form an oxygenated or oxidized substrate or product. An oxidation reaction is typically accompanied by a reduction reaction (hence the term "redox" reaction, for oxidation and reduction). A compound is "oxidized" when it receives oxygen or loses electrons. A compound is "reduced" when it loses oxygen or gains electrons. Some examples of oxidative reactions include but are not limited to the conversion of LAME to HLAME, HLAME to OLAME, OLAME to DDAME and the like.

In particular, the mutant AlkB enzyme may be capable of producing more omega-hydroxy- and/or omega-oxo carboxylic acids and/or esters thereof from carboxylic acids than a wild type AlkB enzyme. There will also be less by products formed.

In one example, the effect of heterologous expression of the AlkB mutants according to any aspect of the present invention may be analysed using *Escherichia coli* as the host cell. These mutant AlkB enzymes may be transformed into *E. coli* and these transformed cells grown under process relevant conditions in a bioreactor in the presence of a substrate such as LAME. Compared to any reference strain expressing wild type AlkB, the mutant strains may be shown to have a significant increase in bioconversion rate of LAME towards HLAME as well as an up to twofold improved ratio of HLAME:DDAME. This ratio may indicate a reduced substrate specificity for HLAME, since HLAME is the precursor of DDAME production in the AlkB reaction cascade. The cells according to any aspect of the present invention may thus give rise to a more energy efficient process in which the space-time-yield as well as product yield may be increased contributing to a more economical polyamide 12 precursor production process.

In particular, the cell and/or method according to any aspect of the present invention may be capable of increasing omega-hydroxylauric acid methylester (HLAME) to dodecanedioic acid monomethylester (DDAME) (HLAME/DDAME) ratio relative to the HLAME/DDAME ratio in a wild type cell. In particular, this method comprises contacting the cell according to any aspect of the present invention with the substrate, LAME. This ratio is calculated by dividing the total amount of HLAME produced in the reaction mixture with the total amount of DDAME produced in the reaction at a given point in time. In particular, the amount of HLAME and/or DDAME may be measured at any given point in time by any known method in the art. More in particular, the concentration of HLAME and/or DDAME may be measured using gas or liquid chromatography coupled with mass spectrometry. The higher the concentration of HLAME, the higher the ratio. In particular, the HLAME/DDAME ratio may at least be 1:1. This in itself may be higher than the wild type enzyme and/or cell. More in particular, the HLAME/DDAME ratio may at least be about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5; 1, 2.6:1, 2.7:1, 2.8:1, 2.9:1, 3:1 and the like. Even more in particular, the HLAME/DDAME ratio may at least be 1.5:1.

In another example, the cell and/or method according to any aspect of the present invention may be capable of increasing omega-aminolauric acid methylester (ALAME) to dodecanedioic acid monomethylester (DDAME) (ALAME/DDAME) ratio relative to the ALAME/DDAME ratio in a wild type cell. In particular, this method comprises contacting the cell according to any aspect of the present invention with the substrate, LAME. This ratio is calculated by dividing the total amount of ALAME produced in the reaction mixture with the total amount of DDAME produced in the reaction at a given point in time. In particular, the amount of ALAME and/or DDAME may be measured at any given point in time by any known method in the art. More in particular, the concentration of ALAME and/or DDAME may be measured using gas or liquid chromatography coupled with mass spectrometry. The higher the concentration of ALAME, the higher the ratio. In particular, the ALAME/DDAME ratio may at least be 1:1. This in itself may be higher than the wild type enzyme and/or cell. More in particular, the ALAME/DDAME ratio may at least be about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5; 1, 2.6:1, 2.7:1, 2.8:1, 2.9:1, 3:1 and the like. Even more in particular, the ALAME/DDAME ratio may at least be 1.5:1.

According to a further aspect of the present invention, there is provided a use of the mutant AlkB enzyme and or cell comprising and expressing the mutant AlkB enzyme according to any aspect of the present invention for catalysing the conversion of lauric acid methyl ester (LAME) to omega-hydroxylauric acid methyl ester (HLAME).

As used herein, "about" or "approximately" shall mean within 20 percent, particularly within 10 percent, and more particularly within 5 percent of a given value or range.

In particular, the mutant AlkB enzyme according to any aspect of the present invention may have a decreased Km value or increased vmax value relative to the wild type AlkB enzyme with respect to the substrate carboxylic acids and/or esters thereof of $C_6$-$C_{14}$ with non-functionalized terminal methyl bonds, such as carboxylic acid methyl, ethyl or propylesters or alkanes, thus resulting in improved activity of mutant AlkB. For example, the mutant AlkB enzyme according to any aspect of the present invention may be capable of recognizing LAME and thus catalyzing the oxidative conversion of substrate LAME to HLAME. In another example, the mutant AlkB enzyme according to any aspect of the present invention may have an increased Km value or decreased vmax value relative to the wild type AlkB enzyme with respect to the substrate OLAME or other substrates with oxo-functionalized terminal bonds, such as omega-oxo carboxylic acid methyl, ethyl or propylesters or alkanals, thus resulting in decreased activity. In a further example, the mutant AlkB enzyme according to any aspect of the present invention may have an increased Km value or decreased vmax value relative to the wild type AlkB enzyme with respect to the substrate HLAME or other substrates with hydroxy-functionalized terminal bonds, such as omega-hydroxy fatty acid methyl, ethyl or propylesters or alkanols, thus resulting in decreased activity.

Accordingly, the mutant AlkB enzyme according to any aspect of the present invention may be useful for the production and/or accumulation of HLAME. In particular, the mutant AlkB enzyme according to any aspect of the present invention may be capable of producing more HLAME relative to the wild type AlkB enzyme and/or this HLAME may not be converted into other downstream products such as OLAME and/or DDAME. Alternatively, the mutant AlkB enzyme according to any aspect of the present invention may be useful for the production and/or accumulation of more HLAME relative to DDAME produced simultaneously as an unwanted by-product. In particular, the mutant AlkB enzyme according to any aspect of the present invention may be capable of producing more HLAME relative to DDAME which may be produced simultaneously as an unwanted by-product, in comparison to the wild type AlkB enzyme. There is thus less wasted resources as a small amount of substrate LAME may be sufficient for the production of large amounts of HLAME relative to the wild type AlkB enzyme. In particular, it could be demonstrated that the AlkB mutants according to any aspect of the present invention proved to have a higher HLAME productivity and additionally a decreased substrate specificity for HLAME and/or OLAME (resulting in an increased HLAME/DDAME product ratio) compared to wildtype AlkB. A similar explanation may be relevant for the increased ALAME/DDAME ratio that may be seen. In one example, endogenous alcohol dehydrogenases found in the cells according to any aspect of the present invention may be involved in the formation of the ALAME thus showing no increase in OLAME.

The cell according to any aspect of the present invention may be further genetically modified to comprise increased expression relative to a wild type cell of an enzyme $E_1$, an ω-transaminase. In particular, enzyme $E_1$ may be capable of catalysing the conversion of the omega-oxocarboxylic acids and/or esters thereof to the corresponding omega-aminocarboxylic acids and/or esters thereof.

The phrase "increased activity of an enzyme", as used herein is to be understood as increased intracellular activity. Basically, an increase in enzymatic activity can be achieved by increasing the copy number of the gene sequence or gene sequences that code for the enzyme, using a strong promoter or employing a gene or allele that codes for a corresponding enzyme with increased activity, altering the codon utilization of the gene, increasing the half-life of the mRNA or of the enzyme in various ways, modifying the regulation of the expression of the gene and optionally by combining these measures. Genetically modified cells used according to any aspect of the present invention are for example produced by transformation, transduction, conjugation or a combination of these methods with a vector that contains the desired gene, an allele of this gene or parts thereof and a vector that makes expression of the gene possible. Heterologous expression is in particular achieved by integration of the gene or of the alleles in the chromosome of the cell or an extrachromosomally replicating vector. In one example, the cell according to any aspect of the present invention may comprise increased expression relative to the wild type cell of ω-transaminase ($E_1$). In particular, the ω-transaminase ($E_1$) is from EC 2.6.1. In particular, the Enzyme $E_1$, may be an aminotransferase ($E_h$) selected from the group consisting of Pseudomonas putida (WP_016502144; WP_016500675.1), Chromobacterium violaceum (NP_901695.1), Rhodobacter sphaeroides 2.4.1 (YP_353455.1) and 3HMU_A, AAD41041.1, AAK15486.1, ABE03917.1, ADR60699.1, ADR61066.1, ADR62525.1, AEL07495.1, CAZ86955.1, EFW82310.1, EFW87681.1, EGC99983.1, EGD03176.1, EGE58369.1, EGH06681.1, EGH08331.1, EGH24301.1, EGH32343.1, EGH46412.1, EGH55033.1, EGH62152.1, EGH67339.1, EGH70821.1, EGH71404.1, EGH78772.1, EGH85312.1, EGH97105.1, EGP57596.1, NP_102850.1, NP_106560.1, NP_248912.1, NP_248990.1, NP_354026.2, NP_421926.1, NP_637699.1, NP_642792.1, NP_744329.1, NP_744732.1, NP_747283.1, NP_795039.1, XP_002943905.1, YP_001021095.1, YP_001059677.1, YP_001061726.1, YP_001066961.1, YP_001074671.1, YP_001120907.1, YP_001140117.1, YP_001170616.1, YP_001185848.1, YP_001188121.1, YP_001233688.1, YP_001268866.1, YP_001270391.1, YP_001345703.1, YP_001412573.1, YP_001417624.1, YP_001526058.1, YP_001579295.1, YP_001581170.1, YP_001668026.1, YP_001669478.1, YP_001671460.1, YP_001685569.1, YP_001747156.1, YP_001749732.1, YP_001765463.1, YP_001766294.1, YP_001790770.1, YP_001808775.1, YP_001809596.1, YP_001859758.1, YP_001888405.1, YP_001903233.1, YP_001977571.1, YP_002229759.1, YP_002231363.1, YP_002280472.1, YP_002297678.1, YP_002543874.1, YP_002549011.1, YP_002796201.1, YP_002801960.1, YP_002875335.1, YP_002897523.1, YP_002912290.1, YP_002974935.1, YP_003060891.1, YP_003264235.1, YP_003552364.1, YP_003578319.1, YP_003591946.1, YP_003607814.1, YP_003641922.1, YP_003674025.1, YP_003692877.1, YP_003755112.1, YP_003896973.1, YP_003907026.1, YP_003912421.1, YP_004086766.1, YP_004142571.1, YP_004147141.1, YP_004228105.1, YP_004278247.1, YP_004305252.1, YP_004356916.1, YP_004364471.1, YP_004378186.1, YP_004379856.1, YP_004390782.1, YP_004472442.1, YP_004590892.1, YP_004612414.1, YP_004676537.1, YP_004693233.1, YP_004701580.1, YP_004701637.1, YP_004704442.1, YP_108931.1, YP_110490.1, YP_168667.1, YP_237931.1, YP_260624.1, YP_262985.1, YP_271307.1, YP_276987.1, YP_334171.1, YP_337172.1, YP_350660.1, YP_351134.1, YP_364386.1, YP_366340.1, YP_369710.1, YP_370582.1, YP_426342.1, YP_440141.1, YP_442361.1, YP_468848.1, YP_521636.1, YP_554363.1, YP_608454.1, YP_610700.1, YP_614980.1, YP_622254.1, YP_625753.1, YP_680590.1, YP_751687.1, YP_767071.1, YP_774090.1, YP_774932.1, YP_788372.1, YP_858562.1, YP_928515.1, YP_983084.1, YP_995622.1, ZP_00948889.1, ZP_00954344.1, ZP_00959736.1, ZP_00998881.1, ZP_01011725.1, ZP_01037109.1, ZP_01058030.1, ZP_01076707.1, ZP_01103959.1, ZP_01167926.1, ZP_01224713.1, ZP_01442907.1, ZP_01446892.1, ZP_01550953.1, ZP_01625518.1, ZP_01745731.1, ZP_01750280.1, ZP_01754305.1, ZP_01763880.1, ZP_01769626.1, ZP_01865961.1, ZP_01881393.1, ZP_01901558.1, ZP_02145337.1, ZP_02151268.1, ZP_02152332.1, ZP_02167267.1, ZP_02190082.1, ZP_02242934.1, ZP_02360937.1, ZP_02367056.1, ZP_02385477.1, ZP_02456487.1, ZP_02883670.1, ZP_03263915.1, ZP_03263990.1, ZP_03400081.1, ZP_03452573.1, ZP_03456092.1, ZP_03517291.1, ZP_03529055.1, ZP_03571515.1, ZP_03572809.1, ZP_03587785.1, ZP_03588560.1, ZP_03697266.1, ZP_03697962.1, ZP_04521092.1, ZP_04590693.1, ZP_04890914.1, ZP_04891982.1, ZP_04893793.1, ZP_04902131.1, ZP_04905327.1, ZP_04941068.1, ZP_04944536.1, ZP_04945255.1, ZP_04959332.1, ZP_04964181.1, ZP_05053721.1, ZP_05063588.1, ZP_05073059.1, ZP_05077806.1, ZP_05082750.1, ZP_05091128.1, ZP_05095488.1, ZP_05101701.1, ZP_05116783.1, ZP_05121836.1, ZP_05127756.1, ZP_05637806.1, ZP_05742087.1, ZP_05783548.1, ZP_05786246.1, ZP_05843149.1, ZP_05945960.1, ZP_06459045.1, ZP_06487195.1, ZP_06492453.1, ZP_06493162.1, ZP_06703644.1, ZP_06731146.1, ZP_06839371.1, ZP_07007312.1, ZP_07266194.1, ZP_07374050.1, ZP_07662787.1, ZP_07778196.1, ZP_07797983.1, ZP_08099459.1, ZP_08138203.1, ZP_08141719.1, ZP_08142973.1, ZP_08177102.1, ZP_08185821.1, ZP_08186468.1, ZP_08208888.1, ZP_08266590.1, ZP_08402041.1, ZP_08406891.1, ZP_08522175.1, ZP_08527488.1, ZP_08631252.1, and ZP_08636687.1.

In particular, the Enzyme $E_1$, may be an aminotransferase selected from the group consisting of NP_901695.1, ZP_03697266.1, AAD41041.1, YP_002796201.1, ZP_03697962.1, YP_001859758.1, YP_002229759.1, YP_001120907.1, YP_110490.1, ZP_04964181.1, YP_774932.1, YP_001766294.1, YP_001581170.1, YP_622254.1, ZP_03588560.1, YP_001809596.1, YP_370582.1, ZP_03572809.1, NP_248990.1, YP_001888405.1, ZP_04905327.1, YP_001061726.1, YP_001668026.1, ZP_01750280.1, ZP_07778196.1, EGH71404.1, NP_744329.1, YP_004147141.1, ADR61066.1, ZP_05783548.1, YP_004701637.1, YP_366340.1, YP_003264235.1, EGD03176.1, YP_001268866.1, ZP_01901558.1, ZP_05121836.1, YP_003692877.1, ZP_03517291.1, YP_002974935.1, YP_001668026.1, ADR61066.1, NP_744329.1, YP_001268866.1, YP_004701637.1, ZP_08142973.1, ADR62525.1, YP_610700.1, NP_747283.1, ADR62525.1, YP_001270391.1, YP_004704442.1, YP_610700.1, YP_001747156.1, ZP_08138203.1, ZP_07266194.1, EGH70821.1, YP_351134.1, EGH32343.1, EGH08331.1, EGH67339.1, YP_001668026.1, YP_004701637.1, YP_237931.1, ZP_03400081.1, ZP_05116783.1, ZP_01550953.1, ZP_07662787.1, YP_928515.1, YP_788372.1, YP_001021095.1, ZP_07797983.1, YP_003578319.1, YP_004305252.1, NP_248912.1, ZP_08636687.1, YP_003912421.1, YP_751687.1, ZP_08142973.1, YP_271307.1, ZP_05082750.1, YP_001417624.1, and YP_353455.1.

Even more in particular, the Enzyme $E_1$ may be transaminase CV2025 from Chromobacterium violaceum DSM30191. The Enzyme $E_1$ according to any aspect of the present invention may comprise at least 50% sequence identity relative to SEQ ID NO:2. More in particular, $E_1$ may comprise a polypeptide with sequence identity of at least 50, 60, 65, 70, 75, 80, 85, 90, 91, 94, 95, 98 or 100% to a polypeptide SEQ ID NO:2.

The enzymes, for example $E_1$ may comprise a polypeptide sequence wherein up to 60%, preferably up to 25%, particularly up to 15%, in particular up to 10, 9, 8, 7, 6, 5, 4, 3, 2 or 1% of the amino acid residues are modified compared to the below reference sequences (accession numbers by deletion, insertion, substitution or a combination thereof and which still possess at least 50%, preferably 65%, particularly preferably 80%, in particular more than 90% of the activity of the protein with the corresponding, below reference sequence, wherein 100% activity of the reference protein is understood to mean the increasing of the activity of the cells used as a biocatalyst, i.e. the quantity of substance converted per unit time based on the cell quantity used (units per gram cell dry weight [U/g CDW]) in comparison to the activity of the biocatalyst in the absence of the reference protein. Modifications of amino acid residues of a given polypeptide sequence which lead to no significant modifications of the properties and function of the given polypeptide are known to those skilled in the art. Thus for example many amino acids can often be exchanged for one another without problems; examples of such suitable amino acid substitutions are: Ala by Ser; Arg by Lys; Asn by Gln or His; Asp by Glu; Cys by Ser; Gln by Asn; Glu by Asp; Gly by Pro; His by Asn or Gln; Ile by Leu or Val; Leu by Met or Val; Lys by Arg or Gln or Glu; Met by Leu or Ile; Phe by Met or Leu or Tyr; Ser by Thr; Thr by Ser; Trp by Tyr; Tyr by Trp or Phe; Val by Ile or Leu. It is also known that modifications, particularly at the N- or C-terminus of a polypeptide in the form of for example amino acid insertions or deletions, often exert no significant influence on the function of the polypeptide.

The expression of the enzymes and genes mentioned above and all mentioned below is determinable by means of 1- and 2-dimensional protein gel separation followed by optical identification of the protein concentration in the gel with appropriate evaluation software.

If the increasing of an enzyme activity is based exclusively on increasing the expression of the corresponding gene, then the quantification of the increasing of the enzyme activity can be simply determined by a comparison of the 1- or 2-dimensional protein separations between wild type and genetically modified cell. A common method for the preparation of the protein gels with bacteria and for identification of the proteins is the procedure described by Hermann et al. (Electrophoresis, 22: 1712-23 (2001). The protein concentration can also be analysed by Western blot hybridization with an antibody specific for the protein to be determined (Sambrook et al., Molecular Cloning: a laboratory manual, 2nd Ed. Cold Spring Harbor Laboratory Press, Cold Spring Harbor, N.Y. USA, 1989) followed by optical evaluation with appropriate software for concentration determination (Lohaus and Meyer (1989) Biospektrum, 5: 32-39; Lottspeich (1999), Angewandte Chemie 111: 2630-2647). This method is also always an option when possible products of the reaction to be catalysed by the enzyme activity to be determined may be rapidly metabolized in the microorganism or else the activity in the wild type is itself too low for it to be possible adequately to determine the enzyme activity to be determined on the basis of the production formation.

According to another aspect of the present invention, there is provided a method of producing at least one omega-hydroxy carboxylic acid and/or ester thereof from at least one carboxylic acid and/or ester thereof as substrate, the method comprising
contacting at least one genetically modified cell expressing a mutant AlkB enzyme with the substrate carboxylic acid and/or ester thereof,
wherein the substrate carboxylic acid and/or ester thereof is a $C_6$-$C_{14}$ carboxylic acid and/or ester thereof; and
the mutant AlkB enzyme comprises at least one point mutation in the wild type sequence of AlkB, wherein the point mutation is at amino acid position selected from the group consisting of V129, L132 and T136 of the wild type AlkB enzyme.

In particular, the point mutation may be selected from the group consisting of V129T, T136A, V129A and L132V.

According to another aspect of the present invention, there is provided a method of producing at least one omega-hydroxy carboxylic acid and/or ester thereof from at least one carboxylic acid and/or ester thereof as substrate, the method comprising
contacting at the cell according to any aspect of the present invention with the substrate carboxylic acid and/or ester thereof.

According to a further aspect of the present invention, there is provided a method of producing at least one omega-aminocarboxylic acid and/or ester thereof from at least one carboxylic acid and/or ester thereof as substrate, the method comprising
contacting the cell according to any aspect of the present invention with the substrate carboxylic acid and/or ester thereof.

According to yet a further aspect of the present invention, there is provided a use of the cell according to any aspect of the present invention for catalysing the conversion of a carboxylic acid and/or ester thereof to a corresponding omega-hydroxy carboxylic acid and/or ester thereof and/or omega-aminocarboxylic acid and/or ester thereof.

The term "contacting", as used herein, means bringing about direct contact between the substrate carboxylic acid and/or ester thereof with the cell according to any aspect of the present invention in an aqueous solution. For example, the cell and carboxylic acid and/or ester thereof may not be in different compartments separated by a barrier such as an inorganic membrane. If the carboxylic acid and/or ester thereof is soluble or made soluble and may be taken up by the cell or can diffuse across biological membranes, it may simply be added to the cell according to any aspect of the present invention in an aqueous solution. In case it is insufficiently soluble, it may be solved in a suitable organic solvent prior to addition to the aqueous solution. The person skilled in the art is able to prepare aqueous solutions of carboxylic acid and/or ester thereof having insufficient solubility by adding suitable organic and/or polar solvents. Such solvents may be provided in the form of an organic phase comprising liquid organic solvent. In one example, the organic solvent or phase may be considered liquid when liquid at 25° C. and standard atmospheric pressure. In another example, the compounds and catalysts may be contacted in vitro, i.e. in a more or less enriched or even purified state, or may be contacted in situ, i.e. they are made as part of the metabolism of the cell and subsequently react inside the cell.

The term "an aqueous solution" is used interchangeably with the term "aqueous medium" and refers to any solution comprising water, mainly water as solvent that may be used to keep the cell according to any aspect of the present invention, at least temporarily, in a metabolically active and/or viable state and comprises, if such is necessary, any additional substrates. The person skilled in the art is familiar with the preparation of numerous aqueous solutions, usually referred to as media that may be used to keep inventive cells, for example LB medium in the case of E. coli. It is advantageous to use as an aqueous solution a minimal medium, i.e. a medium of reasonably simple composition that comprises only the minimal set of salts and nutrients indispensable for keeping the cell in a metabolically active and/or viable state, by contrast to complex mediums, to avoid dispensable contamination of the products with unwanted side products. For example, M9 medium may be used as a minimal medium.

BRIEF DESCRIPTION OF THE FIGURES

FIG. 1A-1D are graphs with HLAME and DDAME concentrations after 29 h of biotransformation. HLAME: omega-hydroxylauric acid methylester; DDAME: dodecanedioic acid monomethylester; OLAME: omega-oxolauric acid methylester; LAME: lauric acid methyl ester.

EXAMPLES

The foregoing describes preferred embodiments, which, as will be understood by those skilled in the art, may be subject to variations or modifications in design, construction or operation without departing from the scope of the claims. These variations, for instance, are intended to be covered by the scope of the claims.

Example 1

Site-Directed Mutagenesis.

The amino acid positions V129, L132 and T136 of AlkB were thought to be involved in substrate recognition and substrate positioning. In order to exchange amino acids in the AlkB enzyme, the corresponding base triplets coding for the desired amino acid were introduced into synthetic oligonucleotides. With the wildtype AlkB gene sequence as a PCR template the mutant AlkB genes (coding for AlkB mutants V129T, V129A and T136A, respectively) were amplified via PCR by the use of the synthetic oligonucleotides. The PCR products were used as insert DNA for the in vitro construction of the expression plasmids. Nucleotide exchanges were introduced via site-directed mutagenesis according to methods known to a person skilled in the art and are shown in the right column of Table 1. These exchanges led to the corresponding AlkB variants shown in the left column of Table 1.

TABLE 1

Nucleotide sequences that were changed to produce specific AlkB mutants

| AlkB enzyme variant | Nucleotide exchange in AlkB coding sequence |
|---|---|
| Wildtype alkB | SEQ ID NO: 3 |
| V129T | G385A, T386C, G387C |
| V129A | T386C, G387C |
| T136A | A406G, A408T |

Example 2

In Vitro Construction of Expression Plasmids

As backbone vector for plasmid construction the plasmid pBT10_alkL [for sequence and construction see Example 1 of WO/2011/131420 (Seq ID No: 8 of WO/2011/131420)] was used. In pBT10_alkL the wildtype AlkB sequence was replaced using the PCR products containing the mutant AlkB genes by the use of the NEBuilder® HiFi DNA Assembly Cloning Kit from NEB (New England Biolabs, Inc.) according to the manufacturer's specifications.

TABLE 2

Plasmids which were used for the construction of E. coli strains. For construction of Plasmid pJ294_alaDH_B.s._TA_C.v.(Ct) see example 1 of WO/2013/024114

| Plasmid | AlkB variant | Transaminase | SEQ ID NO: |
|---|---|---|---|
| pBT10_alkL | Wildtype | — | 5 |
| pBT10_alkL_V129T | V129T | — | 6 |
| pBT10_alkL_T136A | T136A | — | 7 |
| pBT10_alkL_V129A | V129A | — | 8 |
| pJ294_alaDH_B.s._TA_C.v.(Ct) | — | Cv_2025 | 4 |

Example 3

Construction of E. coli strains E. coli W3110 ΔfadE (no b-oxidation) ΔbioH (no methyl ester hydrolysis) was used. The E. coli W3110 ΔbioH strain to knockout the expression of bioH was made using the method disclosed in Example 1 of EP2730655. This strain was then subsequently used to knock out the expression of fadE using the method disclosed in Example 1 of EP2607490. The resultant strain was called E. coli W3110 ΔfadEΔbioH. For the construction of E. coli strains expressing wildtype AlkB, AlkB mutant genes (AlkB variants), and/or transaminase, the E. coli strain W3110 ΔfadEΔbioH was used as host for transformations via electroporation according to methods known to a person skilled in the art. Transformants were selected on LB agar plates containing Kanamycin (50 μg/ml) and/or ampicillin (100 μg/ml). The list of transformants is provided in Table 3.

TABLE 3

E. coli strains obtained by transformation of E. coli W3110 ΔfadEΔbioH with plasmid 1. E. coli strains with both plasmids (plasmid 1 and plasmid 2) are generated via transformation of both plasmids.

| E. coli strain | Plasmid 1 | Plasmid 2 |
|---|---|---|
| EcW3110ΔfadEΔbioH_pBT10_alkL | pBT10_alkL | — |
| EcW3110ΔfadEΔbioH_pBT10_alkL_V129T | pBT10_alkL_V129T | — |
| EcW3110ΔfadEΔbioH_pBT10_alkL_T136A | pBT10_alkL_T136A | — |
| EcW3110ΔfadEΔbioH_pBT10_alkL_V129A | pBT10_alkL_V129A | — |
| EcW3110ΔfadEΔbioH_pBT10_alkL_TA | pBT10_alkL | pJ294_alaDH_B.s._TA_C.v.(Ct) |
| EcW3110ΔfadEΔbioH_pBT10_alkL_V129T_TA | pBT10_alkL_V129T | pJ294_alaDH_B.s._TA_C.v.(Ct) |
| EcW3110ΔfadEΔbioH_pBT10_alkL_T136A_TA | pBT10_alkL_T136A | pJ294_alaDH_B.s._TA_C.v.(Ct) |
| EcW3110ΔfadEΔbioH_pBT10_alkL_V129A_TA | pBT10_alkL_V129A | pJ294_alaDH_B.s._TA_C.v.(Ct) |

Example 4

Activity of AlkB Mutants

The strains of Table 3 were subjected to a fed-batch fermentation in order to investigate their ability to produce omega-hydroxylauric acid methylester, omega-oxolauric acid methylester and dodecanedioic acid monomethylester from methyl laurate (lauric acid methylester). This was carried out in an 8-fold parallel fermentation system from DASGIP®.

For the fermentation, 1 l reactors were used which were equipped with overhead stirrers and impeller turbines. To monitor the process, pH and pO2 were measured directly and continuously during the process using methods known in the art. OTR/CTR measurements served inter alia for estimating the metabolic activity and fitness of the cells.

The pH probes were calibrated by means of a two-point calibration with measurement solutions of pH 4.0 and pH 7.0 according to technical reference of DASGIP. The reactors were provided according to technical reference with the required sensors and connections and the stirrer shaft was installed. The reactors were then filled with 300 ml of water and autoclaved for 20 min at 121° C. in order to ensure sterility. The pO2 probes were polarized overnight (at least 6 h) following connection to the measurement amplifier. The water was then removed under the clean bench and replaced by high-cell-density medium consisting of (NH4)2SO4 1.76 g/l, K2HPO4 19.08 g/l, KH2PO4 12.5 g/l, yeast extracts 6.66 g/l, trisodium citrate dihydrate 11.2 g/l, 17 ml/l of a filter-sterilized 1% strength ammonium iron citrate solution, and 5 ml/l of a filter-sterilized trace element stock solution (consisting of HCl (37%) 36.50 g/l, MnCl2*4H2O 1.91 g/l, ZnSO4*7H2O 1.87 g/l, ethylenediaminetetraacetic acid dihydrate 0.84 g/l, H3BO3 0.30 g/l, Na2MoO4*2H2O 0.25 g/l, CaCl2*2H2O 4.70 g/l, FeSO4*7H2O 17.80 g/l, CuCl2*2H2O 0.15 g/l) with 15 g/l glucose as carbon source (added by metered addition of 30 ml/l of a sterile feed solution consisting of 500 g/l glucose, 1% (w/v) MgSO4*7H2O and 2.2% (w/v) NH4Cl) with 50 mg/l kanamycin.

Subsequently, the pO2 probes were calibrated using a single-point calibration (stirrer: 600 rpm/gassing: 10 sL/h air) to 100% and the feed, correction agent and induction agent stretches were cleaned by means of cleaning-in-place according to technical reference. For this, the tubes were firstly flushed with 70% ethanol, then with 1 M NaOH, then with sterile demineralized water and finally filled with the respective media.

All of the aforementioned *E. coli* strains were cultured firstly from a cryoculture in LB medium (25 ml in a 100 ml baffled shake flask) with 50 mg/l kanamycin overnight at 37° C. and 200 rpm for about 18 h. Then, 2 ml of this culture were transferred for a second preculture stage into 25 ml of high-cell-density medium consisting of (NH4)2SO4 1.76 g/L, K2HPO4 19.08 g/l, KH2PO4 12.5 g/l, yeast extract 6.66 g/l, trisodium citrate dihydrate 11.2 g/l, 17 ml/l of a filter-sterilized 1% strength ammonium iron citrate solution, and 5 ml/l of a filter-sterilized trace element stock solution (consisting of HCl (37%) 36.50 g/l, MnCl2*4H2O 1.91 g/l, ZnSO4*7H2O 1.87 g/l, ethylenediaminetetraacetic acid dihydrate 0.84 g/l, H3BO3 0.30 g/l. Na2MoO4*2H2O 0.25 g/l, CaCl2*2H2O 4.70 g/l, FeSO4*7H2O 17.80 g/l, CuCl2*2H2O 0.15 g/l) with 15 g/l glucose as carbon source (added by metered addition of 30 ml/l of a sterile feed solution consisting of 500 g/l glucose, 1% (w/v) MgSO4*7H2O and 2.2% (w/v) NH4Cl) with the already described antibiotics in a 100 ml shake flask and incubated at 37° C./200 rpm for a further 6 h.

In order to inoculate the reactors with an optical density of 0.1, the $OD_{600}$ of the second preculture stage was measured and the amount of culture required for the inoculation was calculated. The required amount of culture was added with the help of a 5 ml syringe through a septum into the heat-treated and aerated reactor.

The standard program used is shown in Table 4:

TABLE 4

The standard program for determining activity of AlkB mutants

| | DO regulator | | | pH regulator | |
|---|---|---|---|---|---|
| Preset | | 0% | Preset | | 0 ml/h |
| P | | 0.1 | P | | 5 |
| Ti | | 300 s | Ti | | 200 s |
| min | | 0% | min | | 0 ml/h |
| max | | 100% | max | | 40 ml/h |

| N (Rotation) | from | to | XO2 (gas mixture) | from | to | F (gas flow rate) | from | to |
|---|---|---|---|---|---|---|---|---|
| growth and biotransformation | 0% 400 rpm | 30% 1500 rpm | growth and biotransformation | 0% 21% | 100% 21% | growth and biotransformation | 15% 6 sL/h | 80% 72 sL/h |

| Script | |
|---|---|
| Trigger sharp | 31% DO (1/60 h) |
| Induction | 10 h after feed |
| DCPK | start |
| Feed trigger | 50% DO |
| Feed rate | 3 [ml/h] |

The pH was regulated to pH 6.8 on one side with 12.5% strength ammonia solution. During cultivation and biotransformation, the dissolved oxygen (pO2 or DO) in the culture was regulated to at least 30% by means of stirrer feed and gassing rate. Following inoculation, the DO dropped from 100% to this 30%, where it was kept stable for the remainder of the fermentation.

The fermentation was carried out as fed-batch, where the feed start was triggered as delivery to the feed phase with 5 g/l*h glucose feed, consisting of 500 g/l glucose, 1% (w/v) MgSO4*7H2O and 2.2% (w/v) NH4Cl, via the DO peak inducing the end of the batch phase. With feed start, the temperature of 37° C. was lowered to 30° C. 10 h after feed start, the expression of the oxidation genes was induced with 0.025% (v/v) DCPK. The start of the methyl hydroxylaurate production (=start of the biotransformation) was carried out 14 h after feed start. For this purpose, 150 ml of a mixture of methyl laurate and oleic acid (technical-grade 90%) were added as batch to the fermentation broth. The results are shown in FIGS. 1A-1D. All mutants show faster HLAME production compared to control (2-3 fold), faster overall oxidation compared to control (1.5-2 fold) and an improved chemo selectivity (HLAME/DDAME ratio) in all mutants compared to control (1.20-1.75 vs. 0.84). OLAME production is low in all strains (1 g/L in V129A mutant, in all other strains <0.6 g/L).

Example 5

LC-ESI/MS$^2$-Based Quantification of Products

To quantify LAME and HLA in fermentation samples, samples were taken 1/2/4/20/22 h after the start of biotransformation. These samples were prepared for analysis. The quantification of educts, intermediates and products in fermentation samples was carried out by means of LC-ESI/MS$^2$ by reference to an external calibration for all analytes (0.1-50 mg/l) and using the internal standard aminoundecanoic acid (AUD for HLAME), and d3-LAME (for LAME).

The following instruments were used:
HPLC system 1260 (Agilent; Boblingen) with autosampler (G1367E), binary pump (G1312B) and column oven (G1316A)
Mass spectrometer TripelQuad 6410 (Agilent; Boblingen) with ESI source
HPLC column: Kinetex C18, 100×2.1 mm, particle size: 2.6 μm, pore size 100 Å (Phenomenex; Aschaffenburg)
Precolumn: KrudKatcher Ultra HPLC In-Line Filter; 0.5 μm filter depth and 0.004 mm internal diameter (Phenomenex; Aschaffenburg)

The samples were prepared by pipetting 1900 μl of solvent (80% (v/v) acetonitrile, 20% double-distilled H2O (v/v), +0.1% formic acid) and 100 μl sample in a 2-ml reaction vessel. The mixture was vortexed for about 10 seconds and then centrifuged at about 13 000 rpm for 5 min. The clear supernatant was removed using a pipette and, after appropriate dilution, analysed with diluents (80% (v/v) ACN, 20% double-distilled. H2O (v/v), +0.1% formic acid). 100 μL of ISTD were pipetted into each 900 μL sample (10 μL for a sample volume of 90 μL).

The HPLC separation was carried out with the aforementioned column and pre-column. The injection volume was 0.7 μL, the column temperature 50° C., the flow rate 0.6 mL/min. The mobile phase consisted of Eluent A (0.1% strength (v/v) aqueous formic acid) and Eluent B (acetonitrile with 0.1% (v/v) formic acid). The gradient profile as shown in Table 5 was used:

TABLE 5

Gradient profile used in HPLC separation

| Time [min] | Eluent A [%] | Eluent B [%] |
|---|---|---|
| 0 | 77 | 23 |
| 0.3 | 77 | 23 |
| 0.4 | 40 | 60 |
| 2.5 | 40 | 60 |
| 2.6 | 2 | 98 |
| 5.5 | 2 | 98 |
| 5.6 | 77 | 23 |
| 9 | 77 | 23 |

The ESI-MS2 analysis was carried out in the positive mode with the following parameters of the ESI source:

Gas temperature 280° C.

Gas flow rate 11 L/min

Nebulizing pressure 50 psi

Capillary voltage 4000 V

The detection and quantification of the compounds ALAME, DDAME, HLAME, OLAME, LAME, Di-OLAME was carried out with the following MRM parameters, with in each case a product ion being used as qualifier and one as quantifier.

Example 6

Activity of AlkB Mutants with Transaminase

The strains are subjected to a fed-batch fermentation as described in Example 5 in order to investigate their ability to produce omega-hydroxylauric acid methylester, omega-oxolauric acid methylester and dodecanedioic acid monomethylester from methyl laurate (lauric acid methylester). This is carried out in an 8-fold parallel fermentation system from DASGIP as described in example 4.

Example 7

LC-ESI/MS$^2$-Based Quantification of Products of AlkB Mutants with Transaminase The procedure for quantification of educts, intermediates and products is carried out as described in Example 5. Strains EcW3110ΔfadEΔbioH_pBT10_alkL_V129T_TA, EcW3110ΔfadEΔbioH_pBT10_alkL_T136A_TA and EcW3110ΔfadEΔbioH_pBT10_alkL_V129A_TA produce more ALAME relative to DDAME than the reference strain EcW3110ΔfadEΔbioH_pBT10_alkL_TA.

The invention claimed is:

1. A transformed microbial cell expressing a mutant AlkB enzyme, the mutant AlkB enzyme comprising an amino acid sequence as set forth in SEQ ID NO: 1 having point mutations of V129T or V129A and/or T136, wherein the yield the yield of omega-hydroxylated carboxylic acids and/or esters said transformed microbial cell is greater relative to cells expressing wild type AlkB enzyme the amino acid sequence SEQ ID NO: 1.

2. The cell according to claim 1, wherein the point mutation is at amino acid position T136.

3. The cell according to claim 1, wherein the point mutation at amino acid position T136 is T136A.

4. The cell according to claim 1, wherein the point mutation is at amino acid V129T.

5. The cell according to claim 1, wherein the point mutation is at amino acid positions V129 and T136.

6. The cell according to claim 5, wherein the point mutation at amino acid position T136 is T136A.

7. The cell according to claim 1, wherein the cell is further genetically modified to comprise increased expression relative to a wild type cell of an enzyme $E_1$, an ω-transaminase that converts the omega-oxocarboxylic acids and/or esters thereof to the corresponding omega-aminocarboxylic acids and/or esters thereof.

8. A method of producing at least one omega-hydroxy carboxylic acid and/or ester thereof from at least one carboxylic acid and/or ester thereof as substrate, the method comprising
contacting at least one genetically modified cell expressing a mutant AlkB enzyme with the substrate carboxylic acid and/or ester thereof,
wherein the substrate carboxylic acid and/or ester thereof is a $C_6$-$C_{14}$ carboxylic acid and/or ester thereof; and the mutant AlkB enzyme comprises an amino acid sequence as set forth in SEQ ID NO: 1 having point mutations of V129T or V129A and/or T136, wherein the yield of omega-hydroxylated carboxylic acids and/or esters said transformed microbial cell is greater relative to cells expressing wild type AlkB enzyme the amino acid sequence SEQ ID NO: 1.

9. The method according to claim 8 wherein the substrate carboxylic acid and/or ester thereof is lauric acid and/or lauric acid methyl ester (LAME) and the corresponding omega-hydroxy carboxylic acid and/or ester thereof is omega-hydroxylauric acid and/or omega-hydroxylauric acid methyl ester (HLAME).

10. A method of producing at least one omega-hydroxy carboxylic acid and/or ester thereof from at least one carboxylic acid and/or ester thereof as substrate, the method comprising:
contacting the transformed microbial cell according to claim 1 with the substrate carboxylic acid and/or ester thereof.

11. A method of producing at least one omega-aminocarboxylic acid and/or ester thereof from at least one carboxylic acid and/or ester thereof as substrate, the method comprising
contacting the transformed microbial cell according to claim 7 with the substrate carboxylic acid and/or ester thereof.

12. A process for the conversion of a carboxylic acid and/or ester thereof to a corresponding omega-hydroxy carboxylic acid and/or ester thereof and/or omega-amino carboxylic acid and/or ester thereof by contacting the carboxylic acid or ester with a microbial cell, wherein the improvement is the transformed microbial cell of claim 1.

13. The cell according to claim 1, wherein the point mutation is V129A.

* * * * *

SEQUENCE LISTING

<160> NUMBER OF SEQ ID NOS: 8

<210> SEQ ID NO 1
<211> LENGTH: 401
<212> TYPE: PRT
<213> ORGANISM: Pseudomonas putida

<400> SEQUENCE: 1

```
Met Leu Glu Lys His Arg Val Leu Asp Ser Ala Pro Glu Tyr Val Asp
1               5                   10                  15
Lys Lys Lys Tyr Leu Trp Ile Leu Ser Thr Leu Trp Pro Ala Thr Pro
            20                  25                  30
Met Ile Gly Ile Trp Leu Ala Asn Glu Thr Gly Trp Gly Ile Phe Tyr
            35                  40                  45
Gly Leu Val Leu Leu Val Trp Tyr Gly Ala Leu Pro Leu Leu Asp Ala
50                  55                  60
Met Phe Gly Glu Asp Phe Asn Asn Pro Pro Glu Val Val Pro Lys
65              70                  75                  80
Leu Glu Lys Glu Arg Tyr Tyr Arg Val Leu Thr Tyr Leu Thr Val Pro
                85                  90                  95
Met His Tyr Ala Ala Leu Ile Val Ser Ala Trp Trp Val Gly Thr Gln
                100                 105                 110
Pro Met Ser Trp Leu Glu Ile Gly Ala Leu Ala Leu Ser Leu Gly Ile
            115                 120                 125
Val Asn Gly Leu Ala Leu Asn Thr Gly His Glu Leu Gly His Lys Lys
    130                 135                 140
Glu Thr Phe Asp Arg Trp Met Ala Lys Ile Val Leu Ala Val Val Gly
145                 150                 155                 160
Tyr Gly His Phe Phe Ile Glu His Asn Lys Gly His His Arg Asp Val
                165                 170                 175
Ala Thr Pro Met Asp Pro Ala Thr Ser Arg Met Gly Glu Ser Ile Tyr
            180                 185                 190
Lys Phe Ser Ile Arg Glu Ile Pro Gly Ala Phe Ile Arg Ala Trp Gly
            195                 200                 205
Leu Glu Glu Gln Arg Leu Ser Arg Arg Gly Gln Ser Val Trp Ser Phe
210                 215                 220
Asp Asn Glu Ile Leu Gln Pro Met Ile Ile Thr Val Ile Leu Tyr Ala
225                 230                 235                 240
Val Leu Leu Ala Leu Phe Gly Pro Lys Met Leu Val Phe Leu Pro Ile
                245                 250                 255
Gln Met Ala Phe Gly Trp Trp Gln Leu Thr Ser Ala Asn Tyr Ile Glu
            260                 265                 270
His Tyr Gly Leu Leu Arg Gln Lys Met Glu Asp Gly Arg Tyr Glu His
            275                 280                 285
Gln Lys Pro His His Ser Trp Asn Ser Asn His Ile Val Ser Asn Leu
            290                 295                 300
Val Leu Phe His Leu Gln Arg His Ser Asp His Ala His Pro Thr
305                 310                 315                 320
Arg Ser Tyr Gln Ser Leu Arg Asp Phe Pro Gly Leu Pro Ala Leu Pro
                325                 330                 335
Thr Gly Tyr Pro Gly Ala Phe Leu Met Ala Met Ile Pro Gln Trp Phe
            340                 345                 350
Arg Ser Val Met Asp Pro Lys Val Val Asp Trp Ala Gly Gly Asp Leu
            355                 360                 365
Asn Lys Ile Gln Ile Asp Asp Ser Met Arg Glu Thr Tyr Leu Lys Lys
370                 375                 380
Phe Gly Thr Ser Ser Ala Gly His Ser Ser Ser Thr Ser Ala Val Ala
385                 390                 395                 400
Ser
```

<210> SEQ ID NO 2

```
<211> LENGTH: 452
<212> TYPE: PRT
<213> ORGANISM: Pseudomonas putida

<400> SEQUENCE: 2
```

| | | | | | | | | | | | | | | |
|---|---|---|---|---|---|---|---|---|---|---|---|---|---|---|
|Met|Ser|Glu|Gln|Asn|Ser|Gln|Thr|Leu|Ala|Trp|Gln|Ser|Met|Ser|Arg|
|1| | | |5| | | | |10| | | | |15|

Asp His His Leu Ala Pro Phe Ser Asp Val Lys Gln Leu Ala Glu Lys
            20                  25                  30

Gly Pro Arg Ile Ile Thr Ser Ala Lys Gly Val Tyr Leu Trp Asp Ser
        35                  40                  45

Glu Gly Asn Lys Ile Leu Asp Gly Met Ala Gly Leu Trp Cys Val Ala
50                  55                  60

Val Gly Tyr Gly Arg Asp Glu Leu Ala Glu Val Ala Ser Gln Gln Met
65                  70                  75                  80

Lys Gln Leu Pro Tyr Tyr Asn Leu Phe Phe Gln Thr Ala His Pro Pro
                85                  90                  95

Ala Leu Glu Leu Ala Lys Ala Ile Ala Asp Val Ala Pro Gln Gly Met
            100                 105                 110

Asn His Val Phe Phe Thr Gly Ser Gly Ser Glu Gly Asn Asp Thr Val
        115                 120                 125

Leu Arg Met Val Arg His Tyr Trp Ala Leu Lys Gly Lys Lys Asn Lys
130                 135                 140

Asn Val Ile Ile Gly Arg Ile Asn Gly Tyr His Gly Ser Thr Val Ala
145                 150                 155                 160

Gly Ala Ala Leu Gly Gly Met Ser Gly Met His Gln Gln Gly Gly Val
                165                 170                 175

Ile Pro Asp Ile Val His Ile Pro Gln Pro Tyr Trp Phe Gly Glu Gly
            180                 185                 190

Gly Asp Met Thr Glu Ala Asp Phe Gly Val Trp Ala Ala Glu Gln Leu
        195                 200                 205

Glu Lys Lys Ile Leu Glu Val Gly Val Asp Asn Val Ala Ala Phe Ile
210                 215                 220

Ala Glu Pro Ile Gln Gly Ala Gly Gly Val Ile Ile Pro Pro Gln Thr
225                 230                 235                 240

Tyr Trp Pro Lys Val Lys Glu Ile Leu Ala Arg Tyr Asp Ile Leu Phe
                245                 250                 255

Val Ala Asp Glu Val Ile Cys Gly Phe Gly Arg Thr Gly Glu Trp Phe
            260                 265                 270

Gly Thr Asp Tyr Tyr Asp Leu Lys Pro Asp Leu Met Thr Ile Ala Lys
        275                 280                 285

Gly Leu Thr Ser Gly Tyr Ile Pro Met Gly Gly Val Ile Val Arg Asp
290                 295                 300

Glu Val Ala Lys Val Ile Ser Glu Gly Gly Asp Phe Asn His Gly Phe
305                 310                 315                 320

Thr Tyr Ser Gly His Pro Val Ala Ala Val Gly Leu Glu Asn Leu
                325                 330                 335

Arg Ile Leu Arg Asp Glu Gln Ile Ile Gln Gln Val His Asp Lys Thr
            340                 345                 350

Ala Pro Tyr Leu Gln Gln Arg Leu Arg Glu Leu Ala Asp His Pro Leu
        355                 360                 365

Val Gly Glu Val Arg Gly Leu Gly Met Leu Gly Ala Ile Glu Leu Val
370                 375                 380

Lys Asp Lys Ala Thr Arg Ala Arg Tyr Glu Gly Lys Gly Val Gly Met

```
                385                 390                 395                 400
        Ile Cys Arg Gln His Cys Phe Asp Asn Gly Leu Ile Met Arg Ala Val
                            405                 410                 415

Gly Asp Thr Met Ile Ile Ala Pro Pro Leu Val Ile Ser Ile Glu Glu
                    420                 425                 430

Ile Asp Glu Leu Val Glu Lys Ala Arg Lys Cys Leu Asp Leu Thr Tyr
                435                 440                 445

Glu Ala Val Arg
            450

<210> SEQ ID NO 3
<211> LENGTH: 1206
<212> TYPE: DNA
<213> ORGANISM: Pseudomonas putida

<400> SEQUENCE: 3
atgcttgaga acacagagt tctggattcc gctccagagt acgtagataa aaagaaatat      60
ctctggatac tatcaactttt gtggccggct actccgatga tcggaatctg gcttgcaaat    120
gaaactggtt gggggatttt ttatgggctg gtattgctcg tatggtacgg cgcacttcca    180
ttgcttgatg cgatgtttgg tgaggacttt aataatccgc tgaagaagt ggtgccgaaa      240 ctagagaagg agcggtacta tcgagttttg acatatctaa cagttcctat gcattacgct     300
gcattaattg tgtcagcatg gtgggtcgga actcagccaa tgtcttggct tgaaattggt     360
gcgcttgcct tgtcactggg tatcgtgaac ggactagcgc tcaatacagg acacgaactc     420
ggtcacaaga aggagacttt tgatcgttgg atggccaaaa ttgtgttggc tgtcgtaggg     480
tacggtcact tctttattga gcataataag ggtcatcacc gtgatgtcgc tacaccgatg     540
gatcctgcaa catcccggat gggagaaaagc atttataagt tttcaatccg tgagatccca    600
ggagcattta ttcgtgcttg ggggcttgag gaacaacgcc tttcgcgccg tggccaaagc     660
gtttggagtt cgataatga aatcctccaa ccaatgatca tcacagttat tctttacgcc     720
gttctccttg ccttgtttgg acctaagatg ctggtgttcc tgccgattca aatggctttc     780
ggttggtggc agctgaccag tgcgaactat attgaacatt acggcttgct ccgtcaaaaa     840
atggaggacg tcgatatga gcatcaaaag ccgcaccatt cttggaatag taatcacatc     900
gtctctaatc tagtgctgtt ccaccttcag cggcactcgg atcaccacgc gcatccaaca     960
cgttcttatc agtcacttcg ggattttccc ggcctgccgg ctcttccgac gggttaccct    1020
ggtgcatttt tgatggcgat gattcctcag tggtttagat cagttatgga tcccaaggta    1080
gtagattggg ctggtggtga ccttaataag atccaaattg atgattcgat gcgagaaacc    1140
tatttgaaaa aatttggcac tagtagtgct ggtcatagtt cgagtacctc tgcggtagca    1200
tcgtag                                                              1206

<210> SEQ ID NO 4
<211> LENGTH: 6837
<212> TYPE: DNA
<213> ORGANISM: Artificial Sequence
<220> FEATURE:
<223> OTHER INFORMATION: Vector pJ294_alaDH_B.s._TA_C.v

<400> SEQUENCE: 4
ctagattatt aggcgaggcc acgcgctttg agggtctgtt caaattcttc gaggcaacgt      60
tccgccacgg cgagcatttc atccacttcc gcacgggtca taacgagcgg cggtgcagac    120
acaatgtgat cgccgcacgc acgcataatg aggttgttgc gaaaaaaaat atcgcggcag    180
```

```
agggtgccaa tttcgccaaa atccggaaag agttcacgtt tcgctttgtt tttcacgagg    240
gtaaacgcct gcaccatgcc cacgccacgc acatcatcca catgttcaaa acggctaaag    300
gtttcacgcc aacgtttctg catatacggg ccaatatcat ctttcacacg ctgcacaatg    360
ccttcatcac ggagcgccgc aacattcgca tgcgccaccg ccgcacacac cggatggccg    420
ctataggtaa agccatggtt aaaatcaccg cccgcaatga gaccttccgc aacacgtttg    480
cccacaaaca ccgcgccaat cgggagatag ccgctgctga ggccttcgc cgcggtaaag     540 aggtccggct gaaagccaaa atgctgatgg ccaaaccatt cgccggtacg gccaaagccg    600
caaatcactt catccgcaac gaggagcaca tcatatttgc ggcaaatacg ttcaatttcc    660
ggccaatagg ttgccggcgg aacaatcaca ccgcccgcac cctgaatcgg ttcgcccaca    720
aacgccgcca cttatccgc gccgatttcg agaattttt cttcgagcca acgcgccgca      780
accacgccaa attcatccgg ggtcatatct ttgccatgtt tataccacca cggctgttca    840
atatgcgcca tgcccggaat cgggagatcg ccctgttcat gcatatattt catgccgccg    900
aggctcgcac cgccaatggt gctgccgtga tagccgttcc aacggccaat gagggttttt    960
ttttccggtt tgccctgcac atcccaataa cgacgcacca tacgaatcat ggtatccacg   1020
ctttcgctgc cgctgttggt ataaaacaca cgatcaaaac ctgccggggt aacttcggcg   1080
aggaggctgc tgagttccac caccgccgga tgggtggttt taagaaggt gttataaaac    1140 gggagttctt ccatctgacg acgcgccgct tccgcaaaat ctttacggcc atagcccacg   1200
ttcacgcacc agaggcccgc catgccatca ataattttgt tgccttcgct atcccagaga   1260
tacacgcctt cgccacgggt catcacacgc gcacccgcct gattgaggct cgcggtatcg   1320
gtaaacggat ggagatgatg cgccgcatcg agttcacgcc actgagaggt ggtacgctgt   1380
ttctgcatat tatatctcct taaagcttta agcacccgcc acagatgatt catcctgtaa   1440
agctttctcg gcaggaacat actcatagcc tagatctctt gctacagctt cataggtcac   1500
gtgtccgttt gcggtgttta aacccgctct cagtgccgta ttgtctgcga gcgcttttac   1560 tgccccttg ttcgcgattt gcagcgcgta tggaacagta acgttagtca gggcgattgt    1620
tgatgtacga gggactgcgc ctggcatgtt cgctacagca taatgcacaa ccccgtgttt   1680
ttcatatgtt ggctgatcat gtgttgtgat atggtcgaca gtttcgacga tgccgccttg   1740
gtcgatcgct acatcaacaa taactgaacc gggtttcatt tgttttacca tttcctcagt   1800
gacaagagtc ggagctttag cacccggaat taataccgcg caaatgagga gatccgcttc   1860
cgccacagca tcagcaatat tgaccggatt agaaattaac gttttaatct gatggccgaa   1920
gatgtcatca agctggcgca agcggtctgc gtttaagtca atgatcgtca catctgcacc   1980
gaggccgaca gccattttcg ccgcgtttgt cccgacaacg cctcctccga taattgttac   2040
ttttccgcgg gaaacgccag gcaccccggc aagcagaatg cctttccgc ctttaggctt    2100 ttctaagaat tgagcgccga tttgcgctgc cattctgccc gcaacctctg acattggcgt   2160
cagaagaggc aatgtccggc cttcactgac cgtttcatat gcgatggcag ttactccttt   2220
atccttcaag gcctgtgcaa gctcaggctc agctgctaaa tgaaggtacg taaacagcac   2280
aagtcctttg cgaaaataaa catattcttc cggcagcggt tcttttactt tcatgaccat   2340
ttcggcgtcc cagacctgct tcggatcagc aatgatttcc gctcctgctg actcataggc   2400 ttcatttca aatccgcttc caaggcccgc gcctgtttca accagcaccc ggtggccgtt    2460
tgaaatgagc tgagaaacgc cccgggtgt taatgcgaca cggttttcat tgttttttat    2520
```

```
ctctttagga accccctatga tcattatgcc actctccttg gttcctagat cctgtgtgaa    2580
attgttattg ttatccgctc acaattccac acattatacg agccggaagc ataaagtgtc    2640
aagcctgggg tgcctaatga gtgagctaac ttacattaat tgcgttgcgc tcactgcccg    2700
catatctatg agccgggctg aatgatcgac cgagacaggc cctgcgggc tgcaggatcc     2760 gcggccgcct cgagaaaatg aagggaagtt cctatactta ctagagaata ggaacttcta    2820
tagggagtcg aataagggcg acacaaaagg tattctaaat gcataataaa tactgataac    2880
atcttatagt ttgtattata ttttgtatta tcgttgacat gtataatttt gatatcaaaa    2940
actgattttc cctttattat tttcgagatt tattttctta attctcttta acaaactaga    3000
aatattgtat atacaaaaaa tcataaataa tagatgaata gtttaattat aggtgttcat    3060
caatcgaaaa agcaacgtat cttatttaaa gtgcgttgct tttttctcat ttataaggtt    3120
aaataattct catatatcaa gcaaagtgac aggcgccctt aaatattctg acaaatgctc    3180
tttccctaaa ctccccccat aaaaaaaccc gccgaagcgg ttttttacgt tatttgcgga    3240
ttaacgatta ctcgttatca gaaccgccca ggatgcctgg cagttcccta ctctcgccgc    3300
tgcgctcggt cgttcggctg cgggacctca gcgctagcgg agtgtatact ggcttactat    3360
gttggcactg atgagggtgt cagtgaagtg cttcatgtgg caggagaaaa aaggctgcac    3420
cggtgcgtca gcagaatatg tgatacagga tatattccgc ttcctcgctc actgactcgc    3480
tacgctcggt cgttcgactg cggcgagcgg aaatggctta cgaacggggc ggagatttcc    3540
tggaagatgc caggaagata cttaacaggg aagtgagagg gccgcggcaa agccgttttt    3600
ccataggctc cgccccctg acaagcatca cgaaatctga cgctcaaatc agtggtggcg    3660
aaacccgaca ggactataaa gataccaggc gtttccccct ggcggctccc tcgtgcgctc    3720
tcctgttcct gcctttcggt ttaccggtgt cattccgctg ttatggccgc gtttgtctca    3780
ttccacgcct gacactcagt tccgggtagg cagttcgctc caagctggac tgtatgcacg    3840 aacccccccgt tcagtccgac cgctgcgcct tatccggtaa ctatcgtctt gagtccaacc    3900
cggaaagaca tgcaaaagca ccactggcag cagccactgg taattgattt agaggagtta    3960
gtcttgaagt catgcgccgg ttaaggctaa actgaaagga caagttttgg tgactgcgct    4020
cctccaagcc agttacctcg gttcaaagag ttggtagctc agagaacctt cgaaaaaccg    4080
ccctgcaagg cggttttttc gttttcagag caagagatta cgcgcagacc aaaacgatct    4140
caagaagatc atcttattaa tcactgcccg ctttccagtc gggaaacctg tcgtgccagc    4200
tgcattaatg aatcggccaa cgcgcgggga gaggcggttt gcgtattggg cgccagggtg    4260
gttttctttt tcaccagtga gactggcaac agctgattgc ccttcaccgc ctggccctga    4320
gagagttgca gcaagcggtc cacgctggtt tgccccagca ggcgaaaatc ctgtttgatg    4380
gtggttaacg gcgggatata acatgagcta tcttcggtat cgtcgtatcc cactaccgag    4440
atatccgcac caacgcgcag cccggactcg gtaatggcgc gcattgcgcc cagcgccatc    4500
tgatcgttgg caaccagcat cgcagtggga acgatgccct cattcagcat ttgcatggtt    4560
tgttgaaaac cggacatggc actccagtcg ccttcccgtt ccgctatcgg ctgaatttga    4620
ttgcgagtga gatatttatg ccagccagcc agacgcagac gcgccgagac agaacttaat    4680
gggcccgcta acagcgcgat ttgctggtga cccaatgcga ccagatgctc cacgcccagt    4740
cgcgtaccgt cctcatggga gaaaataata ctgttgatgg gtgtctggtc agagacatca    4800
agaaataacg ccggaacatt agtgcaggca gcttccacag caatggcatc ctggtcatcc    4860
agcggatagt taatgatcag cccactgacg cgttgcgcga agagattgtg caccgccgct    4920
```

```
ttacaggctt cgacgccgct tcgttctacc atcgacacca ccacgctggc acccagttga    4980
tcggcgcgag atttaatcgc cgcgacaatt tgcgacggcg cgtgcagggc cagactggag    5040
gtggcaacgc caatcagcaa cgactgtttg cccgccagtt gttgtgccac gcggttggga    5100
atgtaattca gctccgccat cgccgcttcc acttttcccc gcgttttcgc agaaacgtgg    5160
ctggcctggt tcaccacgcg ggaaacggtc tgataagaga caccggcata ctctgcgaca    5220
tcgtataacg ttactggttt catattcacc accctgaatt gactctcttc cgggcgctat    5280
catgccatac cgcgaaaggt tttgcgccat cgatggcgc gccgctttta ccaatgctta    5340
atcagtgagg cacctatctc agcgatctgt ctatttcgtt catccatagt tgcctgactc    5400
cccgtcgtgt agataactac gatacgggag ggcttaccat ctggccccag cgctgcgatg    5460
ataccgcgag aacccgctc accggctccg gatttatcag caataaacca gccagccgga    5520
agggccgagc gcagaagtgg tcctgcaact ttatccgcct ccatccagtc tattaattgt    5580
tgccgggaag ctagagtaag tagttcgcca gttaatagtt tgcgcaacgt tgttgccatc    5640
gctacaggca tcgtggtgtc acgctcgtcg tttggtatgg cttcattcag ctccggttcc    5700
caacgatcaa ggcgagttac atgatccccc atgttgtgca aaaagcggt tagctccttc    5760 ggtcctccga tcgttgtcag aagtaagttg gccgcagtgt tatcactcat ggttatggca    5820
gcactgcata attctcttac tgtcatgcca tccgtaagat gcttttctgt gactggtgag    5880
tactcaacca agtcattctg agaatagtgt atgcggcgac cgagttgctc ttgcccggcg    5940
tcaatacggg ataataccgc gccacatagc agaactttaa aagtgctcat cattggaaaa    6000
cgttcttcgg ggcgaaaact ctcaaggatc ttaccgctgt tgagatccag ttcgatgtaa    6060
cccactcgtg cacccaactg atcttcagca tcttttactt tcaccagcgt ttctgggtga    6120
gcaaaaacag gaaggcaaaa tgccgcaaaa aagggaataa gggcgacacg gaaatgttga    6180
atactcatat tcttcctttt tcaatattat tgaagcattt atcagggtta ttgtctcatg    6240
agcggataca tatttgaatg tatttagaaa aataaacaaa taggggtcag tgttacaacc    6300
aattaaccaa ttctgaacat tatcgcgagc ccatttatac ctgaatatgg ctcataacac    6360
cccttgtttg cctggcggca gtagcgcggt ggtcccacct gaccccatgc cgaactcaga    6420
agtgaaacgc cgtagcgccg atggtagtgt ggggactccc catgcgagag tagggaactg    6480
ccaggcatca aataaaacga aaggctcagt cgaaagactg ggcctttcgc ccgggctaat    6540 tatgggggtgt cgcccttatt cgactctata gtgaagttcc tattctctag tagtataggg    6600
acttctgaag tggggctcga gggccggcc agccgtcaag gttaaggctg ccatatcag    6660 cgactgaaaa gcggccagcc tcggccttgt ttgacgtata accaaagcca ccgggcaacc    6720
aatagccctt gtcacttttg atcaggtaga ccgaccctga agcgcttttt tcgtattcca    6780
taaaaccccc ttctgtgcgt gagtactcat agtataacag gcgtgagtac caacgct      6837
```

<210> SEQ ID NO 5
<211> LENGTH: 12348
<212> TYPE: DNA
<213> ORGANISM: Artificial Sequence
<220> FEATURE:
<223> OTHER INFORMATION: Vector pBT10_alkL

<400> SEQUENCE: 5

```
gggaagccct gcaaagtaaa ctggatggct ttcttgccgc caaggatctg atggcgcagg      60
ggatcaagat ctgatcaaga gacaggatga ggatcgtttc gcatgattga acaagatgga     120
```

```
ttgcacgcag gttctccggc cgcttgggtg gagaggctat tcggctatga ctgggcacaa    180
cagacaatcg gctgctctga tgccgccgtg ttccggctgt cagcgcaggg cgcccggtt     240
cttttttgtca agaccgacct gtccggtgcc ctgaatgaac tgcaggacga ggcagcgcgg   300
ctatcgtggc tggccacgac gggcgttcct tgcgcagctg tgctcgacgt tgtcactgaa    360
gcgggaaggg actggctgct attgggcgaa gtgccgggc aggatctcct gtcatctcac     420
cttgctcctg ccgagaaagt atccatcatg gctgatgcaa tgcggcggct gcatacgctt    480
gatccggcta cctgcccatt cgaccaccaa gcgaaacatc gcatcgagcg agcacgtact    540
cggatggaag ccggtcttgt cgatcaggat gatctggacg aagagcatca ggggctcgcg    600
ccagccgaac tgttcgccag gctcaaggcg cgcatgcccg acggcgagga tctcgtcgtg    660
acccatggcg atgcctgctt gccgaatatc atggtggaaa atggccgctt ttctggattc    720
atcgactgtg gccggctggg tgtggcggac cgctatcagg acatagcgtt ggctacccgt    780
gatattgctg aagagcttgg cggcgaatgg gctgaccgct tcctcgtgct ttacggtatc    840
gccgctcccg attcgcagcg catcgccttc tatcgccttc ttgacgagtt cttctgagcg    900
ggactctggg gttcgaaatg accgaccaat cgattggtaa ctgtcagacc aagtttactc    960
atatatactt tagattgatt taaaacttca tttttaattt aaaaggatct aggtgaagat    1020
ccttttttgat aatctcatga ccaaaatccc ttaacgtgag ttttcgttcc actgagcgtc   1080
agaccccgta gaaaagatca aaggatcttc ttgagatcct ttttttctgc gcgtaatctg    1140
ctgcttgcaa acaaaaaaac caccgctacc agcggtggtt tgtttgccgg atcaagagct    1200
accaactctt tttccgaagg taactggctt cagcagagcg cagataccaa atactgtcct    1260
tctagtgtag ccgtagttag gccaccactt caagaactct gtagcaccgc ctacatacct    1320
cgctctgcta atcctgttac cagtggctgc tgccagtggc gataagtcgt gtcttaccgg    1380
gttggactca agacgatagt taccggataa ggcgcagcgg tcgggctgaa cggggggttc    1440
gtgcacacag cccagcttgg agcgaacgat ctacaccgaa ctgagatacc tacagcgtga    1500
gctatgagaa agcgccacgc ttcccgaagg gagaaaggcg gacaggtatc cggtaagcgg    1560
cagagtcgga acaggagagc gcacgaggga gcttccaggg ggaaacgcct ggtatcttta    1620
tagtcctgtc gggtttcgcc acctctgact tgagcgtcga ttttttgtgat gctcgtcagg   1680
ggggcggagc ctatgaaaaa acgccagcaa cgcggccttt ttacggttcc tggccttttg    1740
ctggcctttt gctcacatgt tctttcctgc gttatcccct gattctgtgg ataaccgtat    1800
taccgccttt gagtgagctg ataccgctcg ccgcagccga acgaccgagc gcagcgagtc    1860
agtgagcgag gaagcggaag agcgcctgat gcggtatttt ctccttacgc atctgtgcgg    1920
tatttcacac cgcataggg atctccaatc gtgccttggc gcagcgacag ccctcggtcc     1980
cccagatagc cattgatctt ctctcgcctg tcccctcagt tcagtaattt cctgcatttg    2040
cctgtttcca gtcggtagat attccacaaa acagcaggga agcagcgctt ttccgctgca    2100
taaccctgct tcggggtcat tatagcgatt ttttcggtat atccatcctt tttcgcacga    2160
tatacaggat tttgccaaag ggttcgtgta gactttcctt ggtgtatcca acggcgtcag    2220
ccgggcagga taggtgaagt aggcccaccc gcgagcgggt gttccttctt cactgtccct    2280
tattcgcacc tggcggtgct caacgggaat cctgctctgc gaggctggcc ggctaccgcc    2340
ggcgtaacag atgagggcaa gcggatggct gatgaaacca agccaaccag gaagggcagc    2400
ccacctatca aggtgtactg ccttccagac gaacgaagag cgattgagga aaaggcggcg    2460
gcggccggca tgagcctgtc ggcctacctg ctggccgtcg gccagggcta caaaatcacg    2520
```

```
ggcgtcgtgg actatgagct cgagaacgct taccgccaac acagcagtgt atttgaataa    2580
gagctcgaac atgatcggat ctcccatttc agcaagggaa atcccaccat agccaccacc    2640
gatttatgtg gcgtagaaaa cggtcatcac caaatatggc aatacttccc cgcccaagcg    2700
ccacataaca gcctgggcca cattttacgc ggtagttccg cacgtacgga gtgcgggggg    2760
cggcaggtaa ctgccgtccc tatcgcgacc gttggttcga gtggctgagc atcattgcta    2820
atcaggtaat tttatactcc ctgcaagcgc accttgacgt ttaggcaaat ttattgtctc    2880
agttgcaatc agtcgctcct gcttgtacgc aaggacttct agttcaagag tttcgttatt    2940
aattgcaaca acgagtttat cgtagtcctt tagagcacca agtccttgca gcgccatccc    3000
tttaagatca gaccagaacc gtggtggggt tggtgctggt gttgatgtgc cacagatgct    3060
acttgcgaca atttgagcgt gtgtaaccgc attatgaatt gtctctaaac gtaccatcgt    3120
tccccaaaaa ggatttctag ccattgcgca gtcgccgatt gcatatatac ttgtatccga    3180
tgtacacatc tgatcatcga ccacaacacc attactcact tcaagggccg cctcagttgc    3240
cagctctagc tctgggatag caccgattcc aactacaatc agatccgcct gaatttcttc    3300
tccactttca agtacgcatt gttcaacatg gccattcctg ccctttatag acgttaattt    3360
cgcattcagc ttgaactcaa ttccttcagc ctccaggcgg gctctgacta agtttgctgc    3420
tgccggcgta accacgcgcg ccattacacg cggggcggct tctatcactg tgaccctctt    3480
ccctaagccc accgcagctg aggcgacttc aagcccgatt actccgccgc ccaacacaac    3540
aacagacgca ctctccacaa gtttcctacg taaattttg gcgtcttcca tactgcgtaa    3600
atagcagacc ccagacagtt cagacccctc gcaggttaac ctacgtgcgc tagcacctgt    3660
tgcaagaatc aattttttcat acgcgtattc ttttccatct ttagaagaaa ctatcttacg    3720
ccccacgtcg attgatacaa tcggtgtatt taacgaaatg gtaatattgt tattcgtata    3780
aaaaccttct ggctttaatg gcactgcgga ttctgcaatc tcacttgtca gaaaagcctt    3840
ggatagagga ggccgctgat aaggcgccac agactccctg ctaaaaatcc taatttcccc    3900
tttataacca tattgacgaa gccagaacgc agcatttact ccagctgtac cagcgccaac    3960
aacaacgatt gccataattc tctctccggt atacttttca ctatatcact taatgccgat    4020
tattttagat aattccttga cgctcagctt caattgttgc ttgcgtgcga ttcactacat    4080
tcaaggtggc aaatattttc ctcatatgcc actttatagc atcttcggtg acatgcatat    4140
ttgttgctat ttgtttgttt gagcaccccct cttttacaag cctcaagaca gcaatctgct    4200
tccgtgtcaa taaagcgtca gctttattct ctgcggactt tccaatctca actattcgcg    4260
gaagactaaa agccccaatc gcttgatcta aattaactgc tgtgaaggct tcacatgaag    4320
ccggtattat tcgctcaatt aaacatactt catcaagaac tgtttgaaag cattgaagct    4380
gttttgctat ctccactgca taaacaatgt taagctgagc cttttttaaa tcaccggcac    4440
ctgcctgcgc tccggccaaa cacaataatc cacggacttc cagctggccc gcgttaattt    4500
tacgggcttg ctgaatagcc aataacgctc tgtgcgcggc actatgaaag ttccgatctc    4560
gggaaagcac tagtgattga acaagcagca ggcgtgcttt tagggggggct gagtgctgtc    4620 cggagaaaat cttatgatct tcaagagttt ttaaattatt tatgcccgtt atgccttgac    4680
agactaagcg ctgatagatc tcaatttggc tcataacttc caatcttggt agatttttt    4740 caaccgcatg cgccttcgcc cactccaata tctcaatgga gccatttagg tcactccttc    4800
caagccgcca agctgacaca gcacggcata cggaaaaaaa cacgtctgtc accccgtgat    4860
```

```
tggaaatgaa ctctaaaatt ttggagagct tttcttctga ggtgtccaag cagcgcaatt    4920
cataatgtaa ctcaagctct agagcgtcaa acattttcga agtaaactcg gattccatca    4980
tctgcgcgcg actgtctgtg cgtgcttgag ttataatctg cctcgcccag cccatttttc    5040
cgcttgctag ggcttgttga aacctcgcga catacagcca accaaaagca aaattttgtt    5100
ttgcaaattt attcacggct tgggcctgag ccagcacctt ctccaactct gcaaatctat    5160
actcactggc aaaataaaa gccaaacagg ttagcgcggc cccttttcca actgcgtttg    5220
aatccccaaa taaactaatc cacttattac agagctcctc actcgaaagc atttcatctt    5280
tcgttgcttt acctattgca agcacaagct gcagccattc cttttcttgc catttatttt    5340
ttttatcgga ttgtgaagat aggtctttaa ttaacttctc tgctcgcgcg ccttgctgac    5400
tgaaatacaa tacccacgcg taactaataa gcactatggg ttttttgtgc caggcctgct    5460
tcggcagctc taacagccac tgtctcagcg catctatttc gccctgacga aatgacaaat    5520
ctaaaattat tctctcagac atgctgactg cccagcgaca gtcattcgcc cgtagggata    5580
ttcgtattgc atactggtat tcacctctac gccaatgcca gaaagctgca cgcttaagca    5640
ggtaggatct tttagcagga ttttcagtcc aagtaatttc tcgtagaaaa ttacgcagta    5700
ctggatgcag tgtaaactgc gctggctcac cgctcacatg gcgaagcaac atgtaattag    5760
tgcttaaata cttaatacat gagaccccat tgacgcattt gaatacataa ttgtattgat    5820
caggcgtcac gaaatcgagc aatgaagaat ttgcaagaaa acacgatag cgctcgggaa    5880 tcgcctcaaa tatttcatcc ctaaagtaat tgtctacttc aactactgct gaaatatgct    5940
tggccggcaa ctcacgcttt aacaaaaaaa ctacaagagc aggccacccc tcaacttctt    6000
gcaccaaggt ctctatctgt tcttcaggaa ctccaagaac agactctgcc tccgctaacg    6060
ccaccgcctc ttctgcgcta aaggccaagt cttctctcggt gtactcccgc atagcgcctg    6120
caagtttaag ctgcgagaac cctttattg tattgcctgc aactgcaaac ctgatatttt    6180
ttggtgtatt taacataaac tccataagtg cgtgcaacaa cggcaagtct aagtcatgat    6240
taatattatc caaacaaact agcgtttcta tctcgttatt cgaggtgctc tgccaaagac    6300
tagatgcaag gtctcgcaag agcgcaggct tgctcacacc ctctctcaca cggctgaatt    6360
ttaccatttc gaaagtttca agctgctcaa taatctctgc gcagatatca aattcactgt    6420
aagaactggc tcttaaagaa agccacactg caggacgtcc ggctgttctg tggcgtagcc    6480
actcgaacgc aagagcaacg gttttcccat atccaggtgg ggctctgtaa aggcatactc    6540
tgggagcggc tccatccgcg atactcaatc ttggccgata tatgcaacta tgaactttgg    6600
cacttactag agtcgtaatt tgatccgctc cgaccttagc gaccgggaaa tcattattta    6660
ttattatttt cattatgcta ttctcgcgcc agctgactgg aaattttcac cataggttac    6720
ggtgttaaat attaaaacta cacttaagtg tagtcggcat gatcggtggt gcaaaatatt    6780
tactagggaa ggtctgaagt aggccgctat ttctggccga cttcggcctt cgccgatttt    6840
gaagacgggc accgggtcaa aatcgaccag atagctcgct catttcggtg ctttcagccg    6900
tcgcgagtag ctcgcggtac ctggcatgct tgcgccagc tcgtgttttt ccagcagacg    6960
acggagcaaa aactacccgt aggtgtagtt ggcgcaagcg tccgattagc tcaggtttaa    7020
gatgtcgaga gtgagagtgg gcggcttaac tttctcagtt aggcataaaa ttacgtctta    7080
aatctcgtag cgactaattt aataaaaatt ggagaattcc atatgcttga gaaacacaga    7140
gttctggatt ccgctccaga gtacgtagat aaaaagaaat atctctggat actatcaact    7200
ttgtggccgg ctactccgat gatcggaatc tggcttgcaa atgaaactgg ttgggggatt    7260
```

```
ttttatgggc tggtattgct cgtatggtac ggcgcacttc cattgcttga tgcgatgttt   7320
ggtgaggact ttaataatcc gcctgaagaa gtggtgccga aactagagaa ggagcggtac   7380
tatcgagttt tgacatatct aacagttcct atgcattacg ctgcattaat tgtgtcagca   7440
tggtgggtcg gaactcagcc aatgtcttgg cttgaaattg gtgcgcttgc cttgtcactg   7500
ggtatcgtga acggactagc gctcaataca ggacacgaac tcggtcacaa gaaggagact   7560
tttgatcgtt ggatggccaa aattgtgttg gctgtcgtag ggtacggtca cttctttatt   7620
gagcataata agggtcatca ccgtgatgtc gctacaccga tggatcctgc aacatcccgg   7680
atgggagaaa gcatttataa gttttcaatc cgtgagatcc caggagcatt tattcgtgct   7740
tgggggcttg aggaacaacg ccttcgcgc cgtggccaaa gcgtttggag tttcgataat   7800
gaaatcctcc aaccaatgat catcacagtt attctttacg ccgttctcct tgccttgttt   7860
ggacctaaga tgctggtgtt cctgccgatt caaatggctt tcggttggtg gcagctgacc   7920
agtgcgaact atattgaaca ttacggcttg ctccgtcaaa aaatggagga cggtcgatat   7980
gagcatcaaa agccgcacca ttcttggaat agtaatcaca tcgtctctaa tctagtgctg   8040
ttccaccttc agcggcactc ggatcaccac gcgcatccaa cacgttctta tcagtcactt   8100
cgggattttc ccggcctgcc ggctcttccg acgggttacc ctggtgcatt tttgatggcg   8160
atgattcctc agtggtttag atcagttatg gatcccaagg tagtagattg gctggtggt    8220
gaccttaata agatccaaat tgatgattcg atgcgagaaa cctatttgaa aaaatttggc   8280
actagtagtg ctggtcatag ttcgagtacc tctgcggtag catcgtagtt atgtgagcac   8340
gcagagcccg gcggtcgata tttacaataa gtgcttcaat tttatgtgcg gcgttgaaag   8400
ctctcacaaa gagtgcactt cgctaaagtg ctgagggttg attgcctctc tgtaattgct   8460
ttgaaggcga cctgctccga tagttacact ctgatgaagt tgtcggagca gcgactaacg   8520
ctgagttaat aggagagtgg gagaatgtca aggtaccagt gtccagattg tcagtatatc   8580
tatgatgaaa ataaggggga gccgcacgaa ggtttccacc cgaacaccag ctggaatgat   8640
atccccaaag attgggcatg cccggactgc gcagttcgag acaaggtgga ctttatcttt   8700
ctcgcggatt ctccctcgaa agaaacacag ctaggggtga atagtcagct tgccaactcg   8760
gaaagtggta tttcagatgc tactccaact ggaatggcag ttttggccgc agaattagtg   8820
atcccactta atcaagaaaa taaaaatgag ggctgtgcgg ctaagactga agttcttgat   8880
caggcgagca ccccacaggt tgtaagaaaa tcttccacaa ggaagaagat gagaaataaa   8940
taacgcaaat ttgccgcaac gcaaataac aatttgacat ggtgatgagt atggctagct   9000
ataaatgccc ggattgtaat tatgtttatg atgagagtgc gggtaatgtg catgaggggt   9060
tttctccagg tacgccttgg caccttattc ctgaggattg tgctgcccc gattgcgccg    9120
ttcgagacaa gcttgacttc atgttaattg agagcggcgt aggtgaaaag ggcgtcacct   9180
caacccatac ttcgccaaat ttatccgagg ttagtggcac aagtttaact gctgaagcag   9240
tggttgcgcc gacaagctta gagaaattgc ctagtgccga cgttaaaggc caagatctat   9300
ataaaactca acctccaagg tctgatgccc aaggcgggaa agcatacttg aagtggatat   9360
gtattacttg tggccatata tatgatgagg cgttgggcga tgaggccgag ggttttactc   9420
caggtactcg ctttgaggat attcctgatg actggtgctg tccggattgc ggggctacga   9480
aagaagacta tgtgctctac gaggaaaagt gaagattaaa acttcaagtc attctaggta   9540
attcaggaca aaataaaaat gaccatacca attagcctag ccaagttaaa ctctagtgcc   9600
```

```
gatacccatt cagcgcttgt cgacctgtaa cgacaacaaa acgagggtag cacaatgagt   9660
ttttctaatt ataaagtaat cgcgatgccg gtgttggttg ctaattttgt tttggggcg    9720 gccactgcat gggcgaatga aaattatccg gcgaaatctg ctggctataa tcagggtgac   9780
tgggtcgcta gcttcaattt ttctaaggtc tatgtgggtg aggagcttgg cgatctaaat   9840
gttggagggg gggctttgcc aaatgctgat gtaagtattg gtaatgatac aacacttacg   9900
tttgatatcg cctattttgt tagctcaaat atagcggtgg attttttgt tggggtgcca    9960 gctagggcta aatttcaagg tgagaaatca atctcctcgc tgggaagagt cagtgaagtt  10020
gattacggcc ctgcaattct ttcgcttcaa tatcattacg atagctttga gcgactttat  10080
ccatatgttg gggttggtgt tggtcgggtg ctattttttg ataaaaccga cggtgctttg  10140
agttcgtttg atattaagga taaatgggcg cctgcttttc aggttggcct tagatatgac  10200
cttggtaact catggatgct aaattcagat gtgcgttata ttcctttcaa aacggacgtc  10260
acaggtactc ttggcccggt tcctgttttct actaaaattg aggttgatcc tttcattctc  10320
agtcttggtg cgtcatatgt tttctaagta atcaggtctg tcactgtcgc aggtcgacct  10380
gcagccaagc ttctgttttg gcggatgaga aagattttc agcctgatac agattaaatc  10440
agaacgcaga agcggtctga taaaacagaa tttgcctggc ggcagtagcg cggtggtccc  10500
acctgacccc atgccgaact cagaagtgaa acgccgtagc gccgatggta gtgtggggtc  10560
tccccatgcg agagtaggga actgccaggc atcaaataaa acgaaaggct cagtcgaaag  10620
actgggcctt tcgttttatc tgttgtttgt cggtgaacgc tctcctgagt aggacaaatc  10680
cgccgggagc ggatttgaac gttgcgaagc aacggcccgg agggtggcgg caggacgcc   10740 cgccataaac tgccaggcat caaattaagc agaaggccat cctgacggat ggccttttg   10800 cgttctaca aactcttttg tttatttttc taaatacatt caaatatgta tccgctcatg   10860
agacaataac cctgataaat gcttcaataa tgcagcctga aaggcaggcc gggccgtggt  10920
ggccacggcc tctaggccag atccagcggc atctgggtta gtcgagcgcg ggccgcttcc  10980
catgtctcac cagggcgagc ctgtttcgcg atctcagcat ctgaaatctt cccggccttg  11040
cgcttcgctg gggccttacc caccgccttg gcgggcttct tcggtccaaa actgaacaac  11100
agatgtgtga ccttgcgccc ggtctttcgc tgcgcccact ccacctgtag cgggctgtgc  11160
tcgttgatct gcgtcacggc tggatcaagc actcgcaact tgaagtcctt gatcgaggga  11220
taccggcctt ccagttgaaa ccactttcgc agctggtcaa tttctatttc gcgctggccg  11280
atgctgtccc attgcatgag cagctcgtaa agcctgatcg cgtgggtgct gtccatcttg  11340
gccacgtcag ccaaggcgta tttggtgaac tgtttggtga gttccgtcag gtacggcagc  11400
atgtctttgg tgaacctgag ttctacacgg ccctcaccct cccggtagat gattgtttgc  11460
acccagccgg taatcatcac actcggtctt ttccccttgc cattgggctc ttgggttaac  11520
cggacttccc gccgtttcag gcgcagggcc gcttctttga gctggttgta ggaagattcg  11580
atagggacac ccgccatcgt cgctatgtcc tccgccgtca ctgaatacat cacttcatcg  11640
gtgacaggct cgctcctctt cacctggcta atacaggcca gaacgatccg ctgttcctga  11700
acactgaggc gatacgcggc ctcgaccagg gcattgcttt tgtaaaccat tggggtgag   11760 gccacgttcg acattccttg tgtataaggg gacactgtat ctgcgtccca caatacaaca  11820
aatccgtccc tttacaacaa caaatccgtc ccttcttaac aacaaatccg tcccttaatg  11880
gcaacaaatc cgtccctttt taaactctac aggccacgga ttacgtggcc tgtagacgtc  11940
ctaaaaggtt taaagggaa aaggaagaaa agggtggaaa cgcaaaaaac gcaccactac   12000
```

| | |
|---|---|
| gtggccccgt tggggccgca tttgtgcccc tgaaggggcg ggggaggcgt ctgggcaatc | 12060 |
| cccgttttac cagtccccta tcgccgcctg agagggcgca ggaagcgagt aatcagggta | 12120 |
| tcgaggcgga ttcacccttg gcgtccaacc agcggcacca gcggcgcctg agaggcgaat | 12180 |
| tgacataagc ctgttcggtt cgtaaactgt aatgcaagta gcgtatgcgc tcacgcaact | 12240 |
| ggtccagaac cttgaccgaa cgcagcggtg gtaacggcgc agtggcggtt ttcatggctt | 12300 |
| gttatgactg tttttttgta cagtctatgc ctcgggcatc caatcgat | 12348 |

<210> SEQ ID NO 6
<211> LENGTH: 12348
<212> TYPE: DNA
<213> ORGANISM: Artificial Sequence
<220> FEATURE:
<223> OTHER INFORMATION: Vector pBT10_alkL_V129T

<400> SEQUENCE: 6

| | |
|---|---|
| gggaagccct gcaaagtaaa ctggatggct ttcttgccgc caaggatctg atggcgcagg | 60 |
| ggatcaagat ctgatcaaga gacaggatga ggatcgtttc gcatgattga acaagatgga | 120 |
| ttgcacgcag gttctccggc cgcttgggtg gagaggctat tcggctatga ctgggcacaa | 180 |
| cagacaatcg gctgctctga tgccgccgtg ttccggctgt cagcgcaggg gcgcccggtt | 240 |
| ctttttgtca agaccgacct gtccggtgcc ctgaatgaac tgcaggacga ggcagcgcgg | 300 |
| ctatcgtggc tggccacgac gggcgttcct tgcgcagctg tgctcgacgt tgtcactgaa | 360 |
| gcgggaaggg actggctgct attgggcgaa gtgccggggc aggatctcct gtcatctcac | 420 |
| cttgctcctg ccgagaaagt atccatcatg gctgatgcaa tgcggcggct gcatacgctt | 480 |
| gatccggcta cctgcccatt cgaccaccaa gcgaaacatc gcatcgagcg agcacgtact | 540 |
| cggatggaag ccggtcttgt cgatcaggat gatctggacg aagagcatca ggggctcgcg | 600 |
| ccagccgaac tgttcgccag gctcaaggcg cgcatgcccg acggcgagga tctcgtcgtg | 660 |
| acccatggcg atgcctgctt gccgaatatc atggtggaaa atggccgctt ttctggattc | 720 |
| atcgactgtg gccggctggg tgtggcggac cgctatcagg acatagcgtt ggctacccgt | 780 |
| gatattgctg aagagcttgg cggcgaatgg gctgaccgct tcctcgtgct ttacggtatc | 840 |
| gccgctcccg attcgcagcg catcgccttc tatcgccttc ttgacgagtt cttctgagcg | 900 |
| ggactctggg gttcgaaatg accgaccaat cgattggtaa ctgtcagacc aagtttactc | 960 |
| atatatactt tagattgatt taaaacttca ttttttaattt aaaaggatct aggtgaagat | 1020 |
| cctttttgat aatctcatga ccaaaatccc ttaacgtgag ttttcgttcc actgagcgtc | 1080 |
| agacccgta gaaaagatca aaggatcttc ttgagatcct ttttttctgc gcgtaatctg | 1140 |
| ctgcttgcaa acaaaaaaac caccgctacc agcggtggtt tgtttgccgg atcaagagct | 1200 |
| accaactctt tttccgaagg taactggctt cagcagagcg cagataccaa atactgtcct | 1260 |
| tctagtgtag ccgtagttag gccaccactt caagaactct gtagcaccgc ctacatacct | 1320 |
| cgctctgcta atcctgttac cagtggctgc tgccagtggc gataagtcgt gtcttaccgg | 1380 |
| gttggactca agacgatagt taccggataa ggcgcagcgg tcgggctgaa cggggggttc | 1440 |
| gtgcacacag cccagcttgg agcgaacgat ctacaccgaa ctgagatacc tacagcgtga | 1500 |
| gctatgagaa agcgccacgc ttcccgaagg gagaaaggcg gacaggtatc cggtaagcgg | 1560 |
| cagagtcgga acaggagagc gcacgaggga gcttccaggg ggaaacgcct ggtatcttta | 1620 |
| tagtcctgtc gggtttcgcc acctctgact tgagcgtcga ttttgtgat gctcgtcagg | 1680 |

-continued

```
ggggcggagc ctatggaaaa acgccagcaa cgcggccttt ttacggttcc tggccttttg    1740
ctggccttt  gctcacatgt tctttcctgc gttatcccct gattctgtgg ataaccgtat    1800
taccgccttt gagtgagctg ataccgctcg ccgcagccga acgaccgagc gcagcgagtc    1860
agtgagcgag gaagcggaag agcgcctgat gcggtatttt ctccttacgc atctgtgcgg    1920
tatttcacac cgcataggg  atctccaatc gtgccttggc gcagcgacag ccctcggtcc    1980
cccagatagc cattgatctt ctctcgcctg tccctcagt  tcagtaattt cctgcatttg    2040
cctgtttcca gtcggtagat attccacaaa acagcaggga agcagcgctt ttccgctgca    2100
taaccctgct cggggtcat  tatagcgatt ttttcggtat atccatcctt tttcgcacga    2160
tatacaggat tttgccaaag ggttcgtgta gactttcctt ggtgtatcca acggcgtcag    2220
ccgggcagga taggtgaagt aggcccaccc gcgagcgggt gttccttctt cactgtccct    2280
tattcgcacc tggcggtgct caacgggaat cctgctctgc gaggctggcc ggctaccgcc    2340
ggcgtaacag atgagggcaa gcggatggct gatgaaacca agccaaccag gaagggcagc    2400
ccacctatca aggtgtactg ccttccagac gaacgaagag cgattgagga aaaggcggcg    2460
gcggccggca tgagcctgtc ggcctacctg ctggccgtcg gccagggcta caaaatcacg    2520
ggcgtcgtgg actatgagct cgagaacgct taccgccaac acagcagtgt atttgaataa    2580
gagctcgaac atgatcggat ctcccatttc agcaagggaa atcccaccat agccaccacc    2640
gatttatgtg gcgtagaaaa cggtcatcac caaatatggc aatacttccc cgcccaagcg    2700
ccacataaca gcctgggcca cattttacgc ggtagttccg cacgtacgga gtgcgggggg    2760
cggcaggtaa ctgccgtccc tatcgcgacc gttggttcga gtggctgagc atcattgcta    2820
atcaggtaat tttatactcc ctgcaagcgc accttgacgt ttaggcaaat ttattgtctc    2880
agttgcaatc agtcgctcct gcttgtacgc aaggacttct agttcaagag tttcgttatt    2940
aattgcaaca acgagtttat cgtagtcctt tagagcacca agtccttgca gcgccatccc    3000
tttaagatca gaccagaacc gtggtggggt tggtgctggt gttgatgtgc cacagatgct    3060
acttgcgaca atttgagcgt gtgtaaccgc attatgaatt gtctctaaac gtaccatcgt    3120
tccccaaaaa ggatttctag ccattgcgca gtcgccgatt gcatatatac ttgtatccga    3180
tgtacacatc tgatcatcga ccacaacacc attactcact tcaagggccg cctcagttgc    3240
cagctctagc tctgggatag caccgattcc aactacaatc agatccgcct gaatttcttc    3300
tccactttca gtacgcatt  gttcaacatg gccattcctg ccctttatag acgttaattt    3360
cgcattcagc ttgaactcaa ttccttcagc ctccaggcgg gctctgacta agttgctgc     3420
tgccggcgta accacgcgcg ccattacacg cggggcggct tctatcactg tgaccctctt    3480
ccctaagccc accgcagctg aggcgacttc aagcccgatt actccgccgc caacacaac     3540
aacagacgca ctctccacaa gtttcctacg taaatttttg gcgtcttcca tactgcgtaa    3600
atagcagacc ccagacagtt cagacccctc gcaggttaac ctacgtgcgc tagcacctgt    3660
tgcaagaatc aattttttcat acgcgtattc ttttccatct ttagaagaaa ctatcttacg    3720
ccccacgtcg attgatacaa tcggtgtatt taacgaaatg gtaatattgt tattcgtata    3780
aaaaccttct ggctttaatg gcactgcgga ttctgcaatc tcacttgtca gaaaagcctt    3840
ggatagagga ggccgctgat aaggcgccac agactccctg ctaaaaatcc taatttcccc    3900
tttataacca tattgacgaa gccagaacgc agcattact  ccagctgtac cagcgccaac    3960
aacaacgatt gccataattc tctctccggt atacttttca ctatatcact taatgccgat    4020
tatttagat  aattccttga cgctcagctt caattgttgc ttgcgtgcga ttcactacat    4080
```

```
tcaaggtggc aaatattttc ctcatatgcc actttatagc atcttcggtg acatgcatat    4140
ttgttgctat ttgtttgttt gagcacccct cttttacaag cctcaagaca gcaatctgct    4200
tccgtgtcaa taaagcgtca gctttattct ctgcggactt tccaatctca actattcgcg    4260
gaagactaaa agccccaatc gcttgatcta aattaactgc tgtgaaggct tcacatgaag    4320
ccggtattat tcgctcaatt aaacatactt catcaagaac tgtttgaaag cattgaagct    4380
gttttgctat ctccactgca taaacaatgt taagctgagc cttttttaaa tcaccggcac    4440
ctgcctgcgc tccggccaaa cacaataatc cacggacttc cagctggccc gcgttaattt    4500
tacgggcttg ctgaatagcc aataacgctc tgtgcgcggc actatgaaag ttccgatctc    4560
gggaaagcac tagtgattga acaagcagca ggcgtgcttt taggggggct gagtgctgtc    4620
cggagaaaat cttatgatct tcaagagttt ttaaattatt tatgcccgtt atgccttgac    4680
agactaagcg ctgatagatc tcaatttggc tcataacttc caatcttggt agatttttt    4740 caaccgcatg cgccttcgcc cactccaata tctcaatgga gccatttagg tcactccttc    4800
caagccgcca agctgacaca gcacggcata cggaaaaaaa cacgtctgtc accccgtgat    4860
tggaaatgaa ctctaaaatt ttggagagct tttcttctga ggtgtccaag cagcgcaatt    4920
cataatgtaa ctcaagctct agagcgtcaa acattttcga agtaaactcg gattccatca    4980
tctgcgcgcg actgtctgtg cgtgcttgag ttataatctg cctcgcccag cccattttc    5040 cgcttgctag ggcttgttga aacctcgcga catacagcca accaaaagca aaattttgtt    5100
ttgcaaattt attcacggct tgggcctgag ccagcacctt ctccaactct gcaaatctat    5160
actcactggc aaaaataaaa gccaaacagg ttagcgcggc ccctttccca actgcgtttg    5220
aatccccaaa taaactaatc cacttattac agagctcctc actcgaaagc atttcatctt    5280
tcgttgcttt acctattgca agcacaagct gcagccattc cttttcttgc catttatttt    5340
ttttatcgga ttgtgaagat aggtctttaa ttaacttctc tgctcgcgcg ccttgctgac    5400
tgaaatacaa tacccacgcg taactaataa gcactatggg tttttttgtgc caggcctgct    5460 tcggcagctc taacagccac tgtctcagcg catctatttc gccctgacga atgacaaat    5520 ctaaaattat tctctcagac atgctgactg cccagcgaca gtcattcgcc cgtagggata    5580
ttcgtattgc atactggtat tcacctctac gccaatgcca gaaagctgca cgcttaagca    5640
ggtaggatct tttagcagga ttttcagtcc aagtaatttc tcgtagaaaa ttacgcagta    5700
ctggatgcag tgtaaactgc gctggctcac cgctcacatg gcgaagcaac atgtaattag    5760
tgcttaaata cttaatacat gagacccat tgacgcattt gaatacataa ttgtattgat    5820
caggcgtcac gaaatcgagc aatgaagaat ttgcaagaaa aacacgatag cgctcgggaa    5880
tcgcctcaaa tatttcatcc ctaaagtaat tgtctacttc aactactgct gaaatatgct    5940
tggccggcaa ctcacgcttt aacaaaaaaa ctacaagagc aggccacccc tcaacttctt    6000
gcaccaaggt ctctatctgt tcttcaggaa ctccaagaac agactctgcc tccgctaacg    6060
ccaccgcctc ttctgcgcta aaggccaagt ctttctcggt gtactcccgc atagcgcctg    6120
caagtttaag ctgcgagaac ccttttattg tattgcctgc aactgcaaac ctgatatttt    6180
ttggtgtatt aacataaac tccataagtg cgtgcaacaa cggcaagtct aagtcatgat    6240
taatattatc caaacaaact agcgtttcta tctcgttatt cgaggtgctc tgccaaagac    6300
tagatgcaag gtctcgcaag agcgcaggct tgctcacacc ctctctcaca cggctgaatt    6360
ttaccatttc gaaagtttca agctgctcaa taatctctgc gcagatatca aattcactgt    6420
```

```
aagaactggc tcttaaagaa agccacactg caggacgtcc ggctgttctg tggcgtagcc    6480
actcgaacgc aagagcaacg gttttcccat atccaggtgg ggctctgtaa aggcatactc    6540
tgggagcggc tccatccgcg atactcaatc ttggccgata tatgcaacta tgaactttgg    6600
cacttactag agtcgtaatt tgatccgctc cgaccttagc gaccgggaaa tcattattta    6660
ttattatttt cattatgcta ttctcgcgcc agctgactgg aaattttcac cataggttac    6720
ggtgttaaat attaaaacta cacttaagtg tagtcggcat gatcggtggt gcaaaatatt    6780
tactagggaa ggtctgaagt aggccgctat ttctggccga cttcggcctt cgccgatttt    6840
gaagacgggc accgggtcaa aatcgaccag atagctcgct catttcggtg ctttcagccg    6900
tcgcgagtag ctcgcggtac ctggcatgct tgcggccagc tcgtgttttt ccagcagacg    6960
acggagcaaa aactacccgt aggtgtagtt ggcgcaagcg tccgattagc tcaggtttaa    7020
gatgtcgaga gtgagagtgg gcggcttaac tttctcagtt aggcataaaa ttacgtctta    7080
aatctcgtag cgactaattt aataaaaatt ggagaattcc atatgcttga gaaacacaga    7140
gttctggatt ccgctccaga gtacgtagat aaaaagaaat atctctggat actatcaact    7200
ttgtggccgg ctactccgat gatcggaatc tggcttgcaa atgaaactgg ttgggggatt    7260
ttttatgggc tggtattgct cgtatggtac ggcgcacttc cattgcttga tgcgatgttt    7320
ggtgaggact ttaataatcc gcctgaagaa gtggtgccga aactagagaa ggagcggtac    7380
tatcgagttt tgacatatct aacagttcct atgcattacg ctgcattaat tgtgtcagca    7440
tggtgggtcg gaactcagcc aatgtcttgg cttgaaattg gtgcgcttgc cttgtcactg    7500
ggtatcacca acggactagc gctcaataca ggacacgaac tcggtcacaa gaaggagact    7560
tttgatcgtt ggatggccaa aattgtgttg gctgtcgtag ggtacggtca cttctttatt    7620
gagcataata agggtcatca ccgtgatgtc gctacaccga tggatcctgc aacatcccgg    7680
atgggagaaa gcatttataa gttttcaatc cgtgagatcc caggagcatt tattcgtgct    7740
tgggggcttg aggaacaacg cctttcgcgc cgtggccaaa gcgtttggag tttcgataat    7800
gaaatcctcc aaccaatgat catcacagtt attctttacg ccgttctcct tgccttgttt    7860
ggacctaaga tgctggtgtt cctgccgatt caaatggctt tcggttggtg gcagctgacc    7920
agtgcgaact atattgaaca ttacggcttg ctccgtcaaa aaatggagga cggtcgatat    7980
gagcatcaaa agccgcacca ttcttggaat agtaatcaca tcgtctctaa tctagtgctg    8040
ttccaccttc agcggcactc ggatcaccac gcgcatccaa cacgttctta tcagtcactt    8100
cgggattttc ccggcctgcc ggctcttccg acgggttacc ctggtgcatt tttgatggcg    8160
atgattcctc agtggtttag atcagttatg gatcccaagg tagtagattg ggctggtggt    8220
gaccttaata agatccaaat tgatgattcg atgcagaaaa cctatttgaa aaaatttggc    8280
actagtagtg ctggtcatag ttcgagtacc tctgcggtag catcgtagtt atgtgagcac    8340
gcagagcccg gcgtcgata tttacaataa gtgcttcaat tttatgtgcg gcgttgaaag    8400
ctctcacaaa gagtgcactt cgctaaagtg ctgagggttg attgcctctc tgtaattgct    8460
ttgaaggcga cctgctccga tagttacact ctgatgaagt tgtcggagca gcgactaacg    8520
ctgagttaat aggagagtgg gagaatgtca aggtaccagt gtccagattg tcagtatatc    8580
tatgatgaaa ataaggggga gccgcacgaa ggtttccacc cgaacaccag ctggaatgat    8640
atccccaaag attgggcatg cccggactgc gcagttcgag acaaggtgga ctttatcttt    8700
ctcgcggatt ctccctcgaa agaaacacag ctaggggtga atagtcagct tgccaactcg    8760
gaaagtggta tttcagatgc tactccaact ggaatggcag ttttggccgc agaattagtg    8820
```

```
atcccactta atcaagaaaa taaaaatgag ggctgtgcgg ctaagactga agttcttgat    8880
caggcgagca ccccacaggt tgtaagaaaa tcttccacaa ggaagaagat gagaaataaa    8940
taacgcaaat ttgccgcaac gcaaaataac aatttgacat ggtgatgagt atggctagct    9000
ataaatgccc ggattgtaat tatgtttatg atgagagtgc gggtaatgtg catgaggggt    9060
tttctccagg tacgccttgg caccttattc ctgaggattg gtgctgcccc gattgcgccg    9120
ttcgagacaa gcttgacttc atgttaattg agagcggcgt aggtgaaaag ggcgtcacct    9180
caacccatac ttcgccaaat ttatccgagg ttagtggcac aagtttaact gctgaagcag    9240
tggttgcgcc gacaagctta gagaaattgc ctagtgccga cgttaaaggc caagatctat    9300
ataaaactca acctccaagg tctgatgccc aaggcgggaa agcatacttg aagtggatat    9360
gtattacttg tggccatata tatgatgagg cgttgggcga tgaggccgag ggttttactc    9420
caggtactcg ctttgaggat attcctgatg actggtgctg tccggattgc ggggctacga    9480
aagaagacta tgtgctctac gaggaaaagt gaagattaaa acttcaagtc attctaggta    9540
attcaggaca aaataaaaat gaccatacca attagcctag ccaagttaaa ctctagtgcc    9600
gatacccatt cagcgcttgt cgacctgtaa cgacaacaaa acgagggtag cacaatgagt    9660
ttttctaatt ataaagtaat cgcgatgccg gtgttggttg ctaattttgt tttggggggcg    9720
gccactgcat gggcgaatga aaattatccg gcgaaatctg ctggctataa tcaggggtgac    9780
tgggtcgcta gcttcaattt ttctaaggtc tatgtgggtg aggagcttgg cgatctaaat    9840
gttggagggg gggcttttgcc aaatgctgat gtaagtattg gtaatgatac aacacttacg    9900
tttgatatcg cctattttgt tagctcaaat atagcggtgg attttttttgt tggggtgcca    9960
gctagggcta aatttcaagg tgagaaatca atctcctcgc tgggaagagt cagtgaagtt    10020
gattacggcc ctgcaattct ttcgcttcaa tatcattacg atagctttga gcgactttat    10080
ccatatgttg gggttggtgt tggtcgggtg ctatttttttg ataaaaccga cggtgctttg    10140
agttcgtttg atattaagga taaatgggcg cctgcttttc aggttggcct tagatatgac    10200
cttggtaact catggatgct aaattcagat gtgcgttata ttcctttcaa aacgacgtc    10260
acaggtactc ttggcccggt tcctgttttct actaaaattg aggttgatcc tttcattctc    10320
agtcttggtg cgtcatatgt tttctaagta atcaggtctg tcactgtcgc aggtcgacct    10380
gcagccaagc ttctgttttg gcggatgaga gaagattttc agcctgatac agattaaatc    10440
agaacgcaga agcggtctga taaaacagaa tttgcctggc ggcagtagcg cggtggtccc    10500
acctgacccc atgccgaact cagaagtgaa acgccgtagc gccgatggta gtgtggggtc    10560
tccccatgcg agagtaggga actgccaggc atcaaataaa acgaaaggct cagtcgaaag    10620
actgggcctt tcgttttatc tgttgtttgt cggtgaacgc tctcctgagt aggacaaatc    10680
cgccgggagc ggatttgaac gttgcgaagc aacggcccgg agggtggcgg caggacgcc     10740
cgccataaac tgccaggcat caaattaagc agaaggccat cctgacggat ggccttttg     10800
cgtttctaca aactcttttg tttattttttc taaatacatt caaatatgta tccgctcatg    10860
agacaataac cctgataaat gcttcaataa tgcagcctga aaggcaggcc gggccgtggt    10920
ggccacggcc tctaggccag atccagcggc atctgggtta gtcgagcgcg ggccgcttcc    10980
catgtctcac cagggcgagc ctgtttcgcg atctcagcat ctgaaatctt cccggccttg    11040
cgcttcgctg gggccttacc caccgccttg gcgggcttct tcggtccaaa actgaacaac    11100
agatgtgtga ccttgcgccc ggtctttcgc tgcgcccact ccacctgtag cgggctgtgc    11160
```

-continued

| | |
|---|---|
| tcgttgatct gcgtcacggc tggatcaagc actcgcaact tgaagtcctt gatcgaggga | 11220 |
| taccggcctt ccagttgaaa ccactttcgc agctggtcaa tttctatttc gcgctggccg | 11280 |
| atgctgtccc attgcatgag cagctcgtaa agcctgatcg cgtgggtgct gtccatcttg | 11340 |
| gccacgtcag ccaaggcgta tttggtgaac tgtttggtga gttccgtcag gtacggcagc | 11400 |
| atgtctttgg tgaacctgag ttctacacgg ccctcaccct cccggtagat gattgtttgc | 11460 |
| acccagccgg taatcatcac actcggtctt ttccccttgc cattgggctc ttgggttaac | 11520 |
| cggacttccc gccgtttcag gcgcagggcc gcttctttga gctggttgta ggaagattcg | 11580 |
| atagggacac ccgccatcgt cgctatgtcc tccgccgtca ctgaatacat cacttcatcg | 11640 |
| gtgacaggct cgctcctctt cacctggcta atacaggcca gaacgatccg ctgttcctga | 11700 |
| acactgaggc gatacgcggc ctcgaccagg gcattgcttt tgtaaaccat tgggggtgag | 11760 |
| gccacgttcg acattccttg tgtataaggg gacactgtat ctgcgtccca caatacaaca | 11820 |
| aatccgtccc tttacaacaa caaatccgtc ccttcttaac aacaaatccg tcccttaatg | 11880 |
| gcaacaaatc cgtccctttt taaactctac aggccacgga ttacgtggcc tgtagacgtc | 11940 |
| ctaaaaggtt taaagggaa aaggaagaaa agggtggaaa cgcaaaaaac gcaccactac | 12000 |
| gtggccccgt tgggggccgca tttgtgcccc tgaaggggcg gggaggcgt ctgggcaatc | 12060 |
| cccgttttac cagtccccta tcgccgcctg agggcgca ggaagcgagt aatcagggta | 12120 |
| tcgaggcgga ttcacccttg gcgtccaacc agcggcacca gcggcgcctg agaggcgaat | 12180 |
| tgacataagc ctgttcggtt cgtaaactgt aatgcaagta gcgtatgcgc tcacgcaact | 12240 |
| ggtccagaac cttgaccgaa cgcagcggtg gtaacgcgc agtggcggtt ttcatggctt | 12300 |
| gttatgactg tttttttgta cagtctatgc ctcgggcatc caatcgat | 12348 |

<210> SEQ ID NO 7
<211> LENGTH: 12348
<212> TYPE: DNA
<213> ORGANISM: Artificial Sequence
<220> FEATURE:
<223> OTHER INFORMATION: Vector pBT10_alkL_T136A

<400> SEQUENCE: 7

| | |
|---|---|
| gggaagccct gcaaagtaaa ctggatggct ttcttgccgc caaggatctg atggcgcagg | 60 |
| ggatcaagat ctgatcaaga gacaggatga ggatcgtttc gcatgattga acaagatgga | 120 |
| ttgcacgcag gttctccggc cgcttgggtg gagaggctat tcggctatga ctgggcacaa | 180 |
| cagacaatcg gctgctctga tgccgccgtg ttccggctgt cagcgcaggg gcgcccggtt | 240 |
| ctttttgtca agaccgacct gtccggtgcc ctgaatgaac tgcaggacga ggcagcgcgg | 300 |
| ctatcgtggc tggccacgac gggcgttcct tgcgcagctg tgctcgacgt tgtcactgaa | 360 |
| gcgggaaggg actggctgct attgggcgaa gtgccggggc aggatctcct gtcatctcac | 420 |
| cttgctcctg ccgagaaagt atccatcatg gctgatgcaa tgcggcggct gcatacgctt | 480 |
| gatccggcta cctgcccatt cgaccaccaa gcgaaacatc gcatcgagcg agcacgtact | 540 |
| cggatggaag ccggtcttgt cgatcaggat gatctggacg aagagcatca ggggctcgcg | 600 |
| ccagccgaac tgttcgccag gctcaaggcg cgcatgcccg acggcgagga tctcgtcgtg | 660 |
| acccatggcg atgcctgctt gccgaatatc atggtggaaa atggccgctt ttctggattc | 720 |
| atcgactgtg gccggctggg tgtggcggac cgctatcagg acatagcgtt ggctacccgt | 780 |
| gatattgctg aagagcttgg cggcgaatgg gctgaccgct tcctcgtgct ttacggtatc | 840 |
| gccgctcccg attcgcagcg catcgccttc tatcgccttc ttgacgagtt cttctgagcg | 900 |

```
ggactctggg gttcgaaatg accgaccaat cgattggtaa ctgtcagacc aagtttactc    960
atatatactt tagattgatt taaaacttca ttttttaattt aaaaggatct aggtgaagat   1020
cctttttgat aatctcatga ccaaaatccc ttaacgtgag ttttcgttcc actgagcgtc   1080
agacccgta gaaaagatca aaggatcttc ttgagatcct ttttttctgc gcgtaatctg    1140
ctgcttgcaa acaaaaaaac caccgctacc agcggtggtt tgtttgccgg atcaagagct   1200
accaactctt tttccgaagg taactggctt cagcagagcg cagataccaa atactgtcct   1260
tctagtgtag ccgtagttag gccaccactt caagaactct gtagcaccgc ctacatacct   1320
cgctctgcta atcctgttac cagtggctgc tgccagtggc gataagtcgt gtcttaccgg   1380
gttggactca agacgatagt taccggataa ggcgcagcgg tcgggctgaa cggggggttc   1440
gtgcacacag cccagcttgg agcgaacgat ctacaccgaa ctgagatacc tacagcgtga   1500
gctatgagaa agcgccacgc ttcccgaagg agaaaggcg gacaggtatc cggtaagcgg    1560
cagagtcgga acaggagagc gcacgaggga gcttccaggg ggaaacgcct ggtatcttta   1620
tagtcctgtc gggtttcgcc acctctgact tgagcgtcga ttttttgtgat gctcgtcagg   1680
ggggcggagc ctatggaaaa acgccagcaa cgcggccttt ttacggttcc tggccttttg   1740
ctggcctttt gctcacatgt tctttcctgc gttatcccct gattctgtgg ataaccgtat   1800
taccgccttt gagtgagctg ataccgctcg ccgcagccga acgaccgagc gcagcgagtc   1860
agtgagcgag gaagcggaag agcgcctgat gcggtatttt ctccttacgc atctgtgcgg   1920
tatttcacac cgcataggg atctccaatc gtgccttggc gcagcgacag ccctcggtcc    1980
cccagatagc cattgatctt ctctcgcctg tcccctcagt tcagtaattt cctgcatttg   2040
cctgttttcca gtcggtagat attccacaaa acagcaggga agcagcgctt ttccgctgca   2100
taaccctgct tcgggtcat tatagcgatt ttttcggtat atccatcctt tttcgcacga    2160
tatacaggat tttgccaaag ggttcgtgta gactttcctt ggtgtatcca acggcgtcag   2220
ccgggcagga taggtgaagt aggcccaccc gcgagcgggt gttccttctt cactgtccct   2280
tattcgcacc tggcggtgct caacgggaat cctgctctgc gaggctggcc ggctaccgcc   2340
ggcgtaacag atgagggcaa gcggatggct gatgaaacca gccaaccag gaagggcagc    2400
ccacctatca aggtgtactg ccttccagac gaacgaagag cgattgagga aaaggcggcg   2460
gcggccggca tgagcctgtc ggcctacctg ctggccgtcg gccagggcta caaaatcacg   2520
ggcgtcgtgg actatgagct cgagaacgct taccgccaac acagcagtgt atttgaataa   2580
gagctcgaac atgatcggat ctcccatttc agcaagggaa atcccaccat agccaccacc   2640
gatttatgtg gcgtagaaaa cggtcatcac caaatatggc aatacttccc cgcccaagcg   2700
ccacataaca gcctgggcca cattttacgc ggtagttccg cacgtacgga gtgcggggg    2760
cggcaggtaa ctgccgtccc tatcgcgacc gttggttcga gtggctgagc atcattgcta   2820
atcaggtaat tttatactcc ctgcaagcgc accttgacgt ttaggcaaat ttattgtctc   2880
agttgcaatc agtcgctcct gcttgtacgc aaggacttct agttcaagag tttcgttatt   2940
aattgcaaca acgagtttat cgtagtcctt tagagcacca agtccttgca gcgccatccc   3000
tttaagatca gaccagaacc gtggtggggt tggtgctggt gttgatgtgc cacagatgct   3060
acttgcgaca atttgagcgt gtgtaaccgc attatgaatt gtctctaaac gtaccatcgt   3120
tccccaaaaa ggatttctag ccattgcgca gtcgccgatt gcatatatac ttgtatccga   3180
tgtacacatc tgatcatcga ccacaacacc attactcact tcaagggccg cctcagttgc   3240
```

```
cagctctagc tctgggatag caccgattcc aactacaatc agatccgcct gaatttcttc    3300
tccactttca agtacgcatt gttcaacatg gccattcctg ccctttatag acgttaattt    3360
cgcattcagc ttgaactcaa ttccttcagc ctccaggcgg gctctgacta agtttgctgc    3420
tgccggcgta accacgcgcg ccattacacg cggggcggct tctatcactg tgaccctctt    3480
ccctaagccc accgcagctg aggcgacttc aagcccgatt actccgccgc caacacaac    3540 aacagacgca ctctccacaa gtttcctacg taaattttg gcgtcttcca tactgcgtaa     3600
atagcagacc ccagacagtt cagacccctc gcaggttaac ctacgtgcgc tagcacctgt    3660
tgcaagaatc aattttttcat acgcgtattc ttttccatct ttagaagaaa ctatcttacg   3720
ccccacgtcg attgatacaa tcggtgtatt aacgaaatg gtaatattgt tattcgtata     3780
aaaaccttct ggctttaatg gcactgcgga ttctgcaatc tcacttgtca gaaaagcctt    3840
ggatagagga ggccgctgat aaggcgccac agactccctg ctaaaaatcc taatttcccc    3900
tttataacca tattgacgaa gccagaacgc agcatttact ccagctgtac cagcgccaac   3960
aacaacgatt gccataattc tctctccggt atacttttca ctatatcact taatgccgat    4020
tattttagat aattccttga cgctcagctt caattgttgc ttgcgtgcga ttcactacat    4080
tcaaggtggc aaatattttc ctcatatgcc actttatagc atcttcggtg acatgcatat    4140
ttgttgctat ttgtttgttt gagcaccct cttttacaag cctcaagaca gcaatctgct    4200
tccgtgtcaa taaagcgtca gctttattct ctgcggactt tccaatctca actattcgcg    4260
gaagactaaa agccccaatc gcttgatcta aattaactgc tgtgaaggct tcacatgaag   4320
ccggtattat tcgctcaatt aaacatactt catcaagaac tgtttgaaag cattgaagct   4380
gttttgctat ctccactgca taaacaatgt taagctgagc ctttttaaa tcaccggcac    4440 ctgcctgcgc tccggccaaa cacaataatc cacggacttc cagctggccc gcgttaattt   4500
tacgggcttg ctgaatagcc aataacgctc tgtgcgcggc actatgaaag ttccgatctc   4560
gggaaagcac tagtgattga acaagcagca ggcgtgcttt tagggggct gagtgctgtc    4620 cggagaaaat cttatgatct tcaagagttt ttaaattatt tatgcccgtt atgccttgac   4680
agactaagcg ctgatagatc tcaatttggc tcataacttc caatcttggt agattttttt   4740
caaccgcatg cgccttcgcc cactccaata tctcaatgga gccatttagg tcactccttc   4800
caagccgcca agctgacaca gcacggcata cggaaaaaaa cacgtctgtc accccgtgat   4860
tggaaatgaa ctctaaaatt ttggagagct tttcttctga ggtgtccaag cagcgcaatt    4920
cataatgtaa ctcaagctct agagcgtcaa acattttcga agtaaactcg gattccatca    4980
tctgcgcgcg actgtctgtg cgtgcttgag ttataatctg cctcgcccag cccatttttc    5040
cgcttgctag gcttgttga aacctcgcga catacagcca accaaaagca aattttgtt     5100 ttgcaaattt attcacggct tgggcctgag ccagcacctt ctccaactct gcaaatctat   5160
actcactggc aaaaataaaa gccaaacagg ttagcgcggc ccttttccca actgcgtttg   5220
aatccccaaa taaactaatc cacttattac agagctcctc actcgaaagc atttcatctt    5280
tcgttgcttt acctattgca agcacaagct gcagccattc cttttcttgc catttatttt    5340
ttttatcgga ttgtgaagat aggtctttaa ttaacttctc tgctcgcgcg ccttgctgac    5400
tgaaatacaa tacccacgcg taactaataa gcactatggg ttttttgtgc caggcctgct    5460
tcggcagctc taacagccac tgtctcagcg catctatttc gccctgacga aatgacaaat    5520
ctaaaattat tctctcagac atgctgactg cccagcgaca gtcattcgcc cgtagggata   5580
ttcgtattgc atactggtat tcacctctac gccaatgcca gaaagctgca cgcttaagca   5640
```

-continued

```
ggtaggatct tttagcagga ttttcagtcc aagtaatttc tcgtagaaaa ttacgcagta      5700
ctggatgcag tgtaaactgc gctggctcac cgctcacatg gcgaagcaac atgtaattag      5760
tgcttaaata cttaatacat gagacccat tgacgcattt gaatacataa ttgtattgat      5820
caggcgtcac gaaatcgagc aatgaagaat ttgcaagaaa acacgatag cgctcgggaa      5880 tcgcctcaaa tatttcatcc ctaaagtaat tgtctacttc aactactgct gaaatatgct      5940
tggccggcaa ctcacgcttt aacaaaaaaa ctacaagagc aggccacccc tcaacttctt      6000
gcaccaaggt ctctatctgt tcttcaggaa ctccaagaac agactctgcc tccgctaacg      6060
ccaccgcctc ttctgcgcta aaggccaagt cttttctcggt gtactcccgc atagcgcctg      6120
caagtttaag ctgcgagaac cctttattg tattgcctgc aactgcaaac ctgatatttt      6180
ttggtgtatt aacataaac tccataagtg cgtgcaacaa cggcaagtct aagtcatgat      6240
taatattatc caaacaaact agcgtttcta tctcgttatt cgaggtgctc tgccaaagac      6300
tagatgcaag gtctcgcaag agcgcaggct tgctcacacc ctctctcaca cggctgaatt      6360
ttaccatttc gaaagtttca agctgctcaa taatctctgc gcagatatca aattcactgt      6420
aagaactggc tcttaaagaa agccacactg caggacgtcc ggctgttctg tggcgtagcc      6480
actcgaacgc aagagcaacg gttttcccat atccaggtgg ggctctgtaa aggcatactc      6540
tgggagcggt ccatccgcg atactcaatc ttggccgata tatgcaacta tgaactttgg      6600
cacttactag agtcgtaatt tgatccgctc cgaccttagc gaccgggaaa tcattattta      6660
ttattatttt cattatgcta ttctcgcgcc agctgactgg aaattttcac cataggttac      6720
ggtgttaaat attaaaacta cacttaagtg tagtcggcat gatcggtggt gcaaaatatt      6780
tactagggaa ggtctgaagt aggccgctat ttctggccga cttcggcctt cgccgatttt      6840
gaagacgggc accgggtcaa aatcgaccag atagctcgct catttcggtg cttttcagccg      6900 tcgcagtag ctcgcggtac ctggcatgct tgcggccagc tcgtgttttt ccagcagacg      6960
acggagcaaa aactacccgt aggtgtagtt ggcgcaagcg tccgattagc tcaggtttaa      7020
gatgtcgaga gtgagagtgg gcggcttaac tttctcagtt aggcataaaa ttacgtctta      7080
aatctcgtag cgactaattt aataaaaatt ggagaattcc atatgcttga gaaacacaga      7140
gttctggatt ccgctccaga gtacgtagat aaaagaaat atctctggat actatcaact      7200
ttgtggccgg ctactccgat gatcggaatc tggcttgcaa atgaaactgg ttgggggatt      7260
ttttatgggc tggtattgct cgtatggtac ggcgcacttc cattgcttga tgcgatgttt      7320
ggtgaggact ttaataatcc gcctgaagaa gtggtgccga actagagaa ggagcggtac      7380 tatcgagttt tgacatatct aacagttcct atgcattacg ctgcattaat tgtgtcagca      7440
tggtgggtcg gaactcagcc aatgtcttgg cttgaaattg gtgcgcttgc cttgtcactg      7500
ggtatcgtga acggactagc gctcaatgct ggacacgaac tcggtcacaa gaaggagact      7560
tttgatcgtt ggatggccaa aattgtgttg gctgtcgtag ggtacggtca cttctttatt      7620
gagcataata agggtcatca ccgtgatgtc gctacaccga tggatcctgc aacatcccgg      7680
atgggagaaa gcatttataa gttttcaatc cgtgagatcc caggagcatt tattcgtgct      7740
tgggggcttg aggaacaacg ccttttcgcgc cgtggccaaa gcgtttggag tttcgataat      7800
gaaatcctcc aaccaatgat catcacagtt attctttacg ccgttctcct tgccttgttt      7860
ggacctaaga tgctggtgtt cctgccgatt caaatggctt tcggttggtg gcagctgacc      7920
agtgcgaact atattgaaca ttacggcttg ctccgtcaaa aaatggagga cggtcgatat      7980
```

```
gagcatcaaa agccgcacca ttcttggaat agtaatcaca tcgtctctaa tctagtgctg    8040
ttccaccttc agcggcactc ggatcaccac gcgcatccaa cacgttctta tcagtcactt    8100
cgggattttc ccggcctgcc ggctcttccg acgggttacc ctggtgcatt tttgatggcg    8160
atgattcctc agtggtttag atcagttatg gatcccaagg tagtagattg gctggtggt    8220 gaccttaata agatccaaat tgatgattcg atgcgagaaa cctatttgaa aaaatttggc    8280
actagtagtg ctggtcatag ttcgagtacc tctgcggtag catcgtagtt atgtgagcac    8340
gcagagcccg gcggtcgata tttacaataa gtgcttcaat tttatgtgcg gcgttgaaag    8400
ctctcacaaa gagtgcactt cgctaaagtg ctgagggttg attgcctctc tgtaattgct    8460
ttgaaggcga cctgctccga tagttacact ctgatgaagt tgtcggagca gcgactaacg    8520
ctgagttaat aggagagtgg gagaatgtca aggtaccagt gtccagattg tcagtatatc    8580
tatgatgaaa ataaggggga gccgcacgaa ggtttccacc cgaacaccag ctggaatgat    8640
atccccaaag attgggcatg cccggactgc gcagttcgag acaaggtgga ctttatcttt    8700
ctcgcggatt ctccctcgaa agaaacacag ctaggggtga atagtcagct tgccaactcg    8760
gaaagtggta tttcagatgc tactccaact ggaatggcag ttttggccgc agaattagtg    8820
atcccactta atcaagaaaa taaaaatgag ggctgtgcgg ctaagactga agttcttgat    8880
caggcgagca ccccacaggt tgtaagaaaa tcttccacaa ggaagaagat gagaaataaa    8940
taacgcaaat ttgccgcaac gcaaataac aatttgacat ggtgatgagt atggctagct    9000
ataaatgccc ggattgtaat tatgtttatg atgagagtgc gggtaatgtg catgaggggt    9060
tttctccagg tacgccttgg caccttattc ctgaggattg tgctgccccc gattgcgccg    9120
ttcgagacaa gcttgacttc atgttaattg agagcggcgt aggtgaaaag ggcgtcacct    9180
caacccatac ttcgccaaat ttatccgagg ttagtgcac aagtttaact gctgaagcag    9240
tggttgcgcc gacaagctta gagaaattgc ctagtgccga cgttaaaggc caagatctat    9300
ataaaactca acctccaagg tctgatgccc aaggcgggaa agcatacttg aagtggatat    9360
gtattacttg tggccatata tatgatgagg cgttgggcga tgaggccgag ggttttactc    9420
caggtactcg ctttgaggat attcctgatg actggtgctg tccggattgc ggggctacga    9480
aagaagacta tgtgctctac gaggaaaagt gaagattaaa acttcaagtc attctaggta    9540
attcaggaca aaataaaaat gaccatacca attagcctag ccaagttaaa ctctagtgcc    9600
gatacccatt cagcgcttgt cgacctgtaa cgacaacaaa acgagggtag cacaatgagt    9660
ttttctaatt ataaagtaat cgcgatgccg gtgttggttg ctaattttgt tttgggggcg    9720
gccactgcat gggcgaatga aaattatccg gcgaaatctg ctggctataa tcagggtgac    9780
tgggtcgcta gcttcaattt ttctaaggtc tatgtgggtg aggagcttgg cgatctaaat    9840
gttggagggg gggctttgcc aaatgctgat gtaagtattg gtaatgatac aacacttacg    9900
tttgatatcg cctattttgt tagctcaaat atagcggtgg atttttttgt tggggtgcca    9960
gctagggcta aatttcaagg tgagaaatca atctcctcgc tgggaagagt cagtgaagtt   10020
gattacggcc ctgcaattct ttcgcttcaa tatcattacg atagctttga gcgactttat   10080
ccatatgttg gggttggtgt tggtcgggtg ctatttttg ataaaaccga cggtgctttg   10140
agttcgtttg atattaagga taaatgggcg cctgcttttc aggttggcct tagatatgac   10200
cttggtaact catggatgct aaattcagat gtgcgttata ttcctttcaa aacggacgtc   10260
acaggtactc ttgccccggt tcctgttcct actaaaattg aggttgatcc tttcattctc   10320
agtcttggtg cgtcatatgt tttctaagta atcaggtctg tcactgtcgc aggtcgacct   10380
```

```
gcagccaagc ttctgttttg gcggatgaga gaagattttc agcctgatac agattaaatc    10440
agaacgcaga agcggtctga taaaacagaa tttgcctggc ggcagtagcg cggtggtccc    10500
acctgacccc atgccgaact cagaagtgaa acgccgtagc gccgatggta gtgtggggtc    10560
tccccatgcg agagtaggga actgccaggc atcaaataaa acgaaaggct cagtcgaaag    10620
actgggcctt tcgttttatc tgttgtttgt cggtgaacgc tctcctgagt aggacaaatc    10680
cgccgggagc ggatttgaac gttgcgaagc aacggcccgg agggtggcgg gcaggacgcc    10740
cgccataaac tgccaggcat caaattaagc agaaggccat cctgacggat ggcctttttg    10800
cgtttctaca aactcttttg tttattttc taaatacatt caaatatgta tccgctcatg    10860
agacaataac cctgataaat gcttcaataa tgcagcctga aaggcaggcc gggccgtggt    10920
ggccacggcc tctaggccag atccagcggc atctgggtta gtcgagcgcg gccgcttcc    10980
catgtctcac cagggcgagc ctgtttcgcg atctcagcat ctgaaatctt cccggccttg    11040
cgcttcgctg ggccttacc caccgccttg gcgggcttct tcggtccaaa actgaacaac    11100
agatgtgtga ccttgcgccc ggtctttcgc tgcgcccact ccacctgtag cgggctgtgc    11160
tcgttgatct gcgtcacggc tggatcaagc actcgcaact tgaagtcctt gatcgaggga    11220
taccggcctt ccagttgaaa ccactttcgc agctggtcaa tttctatttc gcgctggccg    11280
atgctgtccc attgcatgag cagctcgtaa agcctgatcg cgtgggtgct gtccatcttg    11340
gccacgtcag ccaaggcgta tttggtgaac tgtttggtga gttccgtcag gtacggcagc    11400
atgtctttgg tgaacctgag ttctacacgg ccctcacccctcccggtagat gattgtttgc    11460
acccagccgg taatcatcac actcggtctt ttccccttgc cattgggctc ttgggttaac    11520
cggacttccc gccgtttcag gcgcagggcc gcttctttga gctggttgta ggaagattcg    11580
atagggacac ccgccatcgt cgctatgtcc tccgccgtca ctgaatacat cacttcatcg    11640
gtgacaggct cgctcctctt cacctggcta atacaggcca gaacgatccg ctgttcctga    11700
acactgaggc gatacgcggc ctcgaccagg gcattgcttt tgtaaaccat tggggtgag    11760
gccacgttcg acattccttg tgtataaggg gacactgtat ctgcgtccca caatacaaca    11820
aatccgtccc tttacaacaa caaatccgtc ccttcttaac aacaaatccg tcccttaatg    11880
gcaacaaatc cgtccctttt taaactctac aggccacgga ttacgtggcc tgtagacgtc    11940
ctaaaaggtt taaagggaa aaggaagaaa agggtggaaa cgcaaaaaac gcaccactac    12000
gtggccccgt tggggccgca tttgtgcccc tgaaggggcg ggggaggcgt ctgggcaatc    12060
cccgttttac cagtccccta tcgccgcctg agagggcgca ggaagcgagt aatcagggta    12120
tcgaggcgga ttcacccttg gcgtccaacc agcggcacca gcggcgcctg agaggcgaat    12180
tgacataagc ctgttcggtt cgtaaactgt aatgcaagta gcgtatgcgc tcacgcaact    12240
ggtccagaac cttgaccgaa cgcagcggtg gtaacggcgc agtggcggtt ttcatggctt    12300
gttatgactg ttttttgta cagtctatgc ctcgggcatc caatcgat              12348
```

<210> SEQ ID NO 8
<211> LENGTH: 12348
<212> TYPE: DNA
<213> ORGANISM: Artificial Sequence
<220> FEATURE:
<223> OTHER INFORMATION: Vector pBT10_alkL_V129A

<400> SEQUENCE: 8

```
gggaagccct gcaaagtaaa ctggatggct ttcttgccgc caaggatctg atggcgcagg    60
```

```
ggatcaagat ctgatcaaga gacaggatga ggatcgtttc gcatgattga acaagatgga    120
ttgcacgcag gttctccggc cgcttgggtg gagaggctat tcggctatga ctgggcacaa    180
cagacaatcg gctgctctga tgccgccgtg ttccggctgt cagcgcaggg gcgcccggtt    240 cttttttgtca agaccgacct gtccggtgcc ctgaatgaac tgcaggacga ggcagcgcgg    300
ctatcgtggc tggccacgac gggcgttcct tgcgcagctg tgctcgacgt tgtcactgaa    360
gcgggaaggg actggctgct attgggcgaa gtgccggggc aggatctcct gtcatctcac    420
cttgctcctg ccgagaaagt atccatcatg gctgatgcaa tgcggcggct gcatacgctt    480
gatccggcta cctgcccatt cgaccaccaa gcgaaacatc gcatcgagcg agcacgtact    540
cggatggaag ccggtcttgt cgatcaggat gatctggacg aagagcatca ggggctcgcg    600
ccagccgaac tgttcgccag gctcaaggcg cgcatgcccg acggcgagga tctcgtcgtg    660
acccatggcg atgcctgctt gccgaatatc atggtggaaa atggccgctt ttctggattc    720
atcgactgtg gccggctggg tgtggcggac cgctatcagg acatagcgtt ggctacccgt    780
gatattgctg aagagcttgg cggcgaatgg gctgaccgct tcctcgtgct ttacggtatc    840
gccgctcccg attcgcagcg catcgccttc tatcgccttc ttgacgagtt cttctgagcg    900
ggactctggg gttcgaaatg accgaccaat cgattggtaa ctgtcagacc aagtttactc    960
atatatactt tagattgatt taaaacttca tttttaattt aaaaggatct aggtgaagat   1020
cctttttgat aatctcatga ccaaaatccc ttaacgtgag ttttcgttcc actgagcgtc   1080 agacccgta gaaaagatca aggatcttc ttgagatcct ttttttctgc gcgtaatctg   1140
ctgcttgcaa acaaaaaaac caccgctacc agcggtggtt tgtttgccgg atcaagagct   1200
accaactctt tttccgaagg taactggctt cagcagagcg cagataccaa atactgtcct   1260
tctagtgtag ccgtagttag gccaccactt caagaactct gtagcaccgc ctacatacct   1320
cgctctgcta atcctgttac cagtggctgc tgccagtggc gataagtcgt gtcttaccgg   1380
gttggactca agacgatagt taccggataa ggcgcagcgg tcgggctgaa cggggggttc   1440
gtgcacacag cccagcttgg agcgaacgat ctacaccgaa ctgagatacc tacagcgtga   1500
gctatgagaa agcgccacgc ttcccgaagg agaaaggcg gacaggtatc cggtaagcgg   1560
cagagtcgga acaggagagc gcacgaggga gcttccaggg ggaaacgcct ggtatcttta   1620
tagtcctgtc gggtttcgcc acctctgact tgagcgtcga ttttttgtgat gctcgtcagg   1680 ggggcggagc ctatggaaaa acgccagcaa cgcggccttt ttacggttcc tggccttttg   1740
ctggcctttt gctcacatgt tctttcctgc gttatcccct gattctgtgg ataaccgtat   1800
taccgccttt gagtgagctg ataccgctcg ccgcagccga acgaccgagc gcagcgagtc   1860
agtgagcgag gaagcggaag agcgcctgat gcggtatttt ctccttacgc atctgtgcgg   1920
tatttcacac cgcatagggg atctccaatc gtgccttggc gcagcgacag ccctcggtcc   1980
cccagatagc cattgatctt ctctcgcctg tccctcagt tcagtaattt cctgcatttg   2040
cctgtttcca gtcggtagat attccacaaa acagcaggga agcagcgctt ttccgctgca   2100
taaccctgct tcggggtcat tatagcgatt ttttcggtat atccatcctt tttcgcacga   2160
tatacaggat tttgccaaag ggttcgtgta gactttcctt ggtgtatcca acggcgtcag   2220
ccgggcagga taggtgaagt aggcccaccc gcgagcgggt gttccttctt cactgtccct   2280
tattcgcacc tggcggtgct caacgggaat cctgctctgc gaggctggcc ggctaccgcc   2340
ggcgtaacag atgagggcaa gcggatggct gatgaaacca agccaaccag gaagggcagc   2400
ccacctatca aggtgtactg ccttccagac gaacgaagag cgattgagga aaaggcggcg   2460
```

```
gcggccggca tgagcctgtc ggcctacctg ctggccgtcg gccagggcta caaaatcacg   2520
ggcgtcgtgg actatgagct cgagaacgct taccgccaac acagcagtgt atttgaataa   2580
gagctcgaac atgatcggat ctcccatttc agcaagggaa atcccaccat agccaccacc   2640
gatttatgtg gcgtagaaaa cggtcatcac caaatatggc aatacttccc cgcccaagcg   2700
ccacataaca gcctgggcca cattttacgc ggtagttccg cacgtacgga gtgcgggggg   2760
cggcaggtaa ctgccgtccc tatcgcgacc gttggttcga gtggctgagc atcattgcta   2820
atcaggtaat tttatactcc ctgcaagcgc accttgacgt ttaggcaaat ttattgtctc   2880
agttgcaatc agtcgctcct gcttgtacgc aaggacttct agttcaagag tttcgttatt   2940
aattgcaaca acgagtttat cgtagtcctt tagagcacca agtccttgca gcgccatccc   3000
tttaagatca gaccagaacc gtggtggggt tggtgctggt gttgatgtgc cacagatgct   3060
acttgcgaca atttgagcgt gtgtaaccgc attatgaatt gtctctaaac gtaccatcgt   3120
tccccaaaaa ggatttctag ccattgcgca gtcgccgatt gcatatatac ttgtatccga   3180
tgtacacatc tgatcatcga ccacaacacc attactcact tcaagggccg cctcagttgc   3240
cagctctagc tctgggatag caccgattcc aactacaatc agatccgcct gaatttcttc   3300
tccactttca agtacgcatt gttcaacatg gccattcctg ccctttatag acgttaattt   3360
cgcattcagc ttgaactcaa ttccttcagc ctccaggcgg gctctgacta agtttgctgc   3420
tgccggcgta accacgcgcg ccattacacg cggggcggct tctatcactg tgaccctctt   3480
ccctaagccc accgcagctg aggcgacttc aagcccgatt actccgccgc caacacaac   3540 aacagacgca ctctccacaa gtttcctacg taaattttg gcgtcttcca tactgcgtaa   3600
atagcagacc ccagacagtt cagacccctc gcaggttaac ctacgtgcgc tagcacctgt   3660
tgcaagaatc aattttttcat acgcgtattc ttttccatct ttagaagaaa ctatcttacg   3720
ccccacgtcg attgatacaa tcggtgtatt taacgaaatg gtaatattgt tattcgtata   3780
aaaaccttct ggctttaatg gcactgcgga ttctgcaatc tcacttgtca gaaaagcctt   3840
ggatagagga ggccgctgat aaggcgccac agactccctg ctaaaaatcc taatttcccc   3900
tttataacca tattgacgaa gccagaacgc agcatttact ccagctgtac cagcgccaac   3960
aacaacgatt gccataattc tctctccggt atacttttca ctatatcact taatgccgat   4020
tattttagat aattccttga cgctcagctt caattgttgc ttgcgtgcga ttcactacat   4080
tcaaggtggc aaatattttc ctcatatgcc actttatagc atcttcggtg acatgcatat   4140
ttgttgctat ttgtttgttt gagcacccct cttttacaag cctcaagaca gcaatctgct   4200
tccgtgtcaa taaagcgtca gctttattct ctgcggactt tccaatctca actattcgcg   4260
gaagactaaa agcccaatc gcttgatcta aattaactgc tgtgaaggct tcacatgaag   4320
ccggtattat tcgctcaatt aaacatactt catcaagaac tgtttgaaag cattgaagct   4380
gttttgctat ctccactgca taaacaatgt taagctgagc cttttttaaa tcaccggcac   4440
ctgcctgcgc tccggccaaa cacaataatc cacggacttc cagctggccc gcgttaattt   4500
tacgggcttg ctgaatagcc aataacgctc tgtgcgcggc actatgaaag ttccgatctc   4560
gggaaagcac tagtgattga acaagcagca ggcgtgcttt tagggggggct gagtgctgtc   4620 cggagaaaat cttatgatct tcaagagttt ttaaattatt tatgcccgtt atgccttgac   4680
agactaagcg ctgatagatc tcaatttggc tcataacttc caatcttggt agatttttt   4740 caaccgcatg cgccttcgcc cactccaata tctcaatgga gccatttagg tcactccttc   4800
```

-continued

```
caagccgcca agctgacaca gcacggcata cggaaaaaaa cacgtctgtc accccgtgat    4860
tggaaatgaa ctctaaaatt ttggagagct tttcttctga ggtgtccaag cagcgcaatt    4920
cataatgtaa ctcaagctct agagcgtcaa acattttcga agtaaactcg gattccatca    4980
tctgcgcgcg actgtctgtg cgtgcttgag ttataatctg cctcgcccag cccattttc     5040 cgcttgctag ggcttgttga aacctcgcga catacagcca accaaaagca aaattttgtt    5100
ttgcaaattt attcacggct tgggcctgag ccagcacctt ctccaactct gcaaatctat    5160
actcactggc aaaaataaaa gccaaacagg ttagcgcggc ccctttttcca actgcgtttg    5220 aatccccaaa taaactaatc cacttattac agagctcctc actcgaaagc atttcatctt    5280
tcgttgcttt acctattgca agcacaagct gcagccattc cttttcttgc catttatttt    5340
ttttatcgga ttgtgaagat aggtctttaa ttaacttctc tgctcgcgcg ccttgctgac    5400
tgaaatacaa tacccacgcg taactaataa gcactatggg tttttttgtgc caggcctgct   5460 tcggcagctc taacagccac tgtctcagcg catctatttc gccctgacga aatgacaaat    5520
ctaaaattat tctctcagac atgctgactg cccagcgaca gtcattcgcc cgtagggata    5580
ttcgtattgc atactggtat tcacctctac gccaatgcca gaaagctgca cgcttaagca    5640
ggtaggatct tttagcagga ttttcagtcc aagtaatttc tcgtagaaaa ttacgcagta    5700
ctggatgcag tgtaaactgc gctggctcac cgctcacatg gcgaagcaac atgtaattag    5760
tgcttaaata cttaatacat gagacccat tgacgcattt gaatacataa ttgtattgat     5820
caggcgtcac gaaatcgagc aatgaagaat ttgcaagaaa acacgatag cgctcgggaa     5880 tcgcctcaaa tatttcatcc ctaaagtaat tgtctacttc aactactgct gaaatatgct    5940
tggccggcaa ctcacgcttt aacaaaaaaa ctacaagagc aggccacccc tcaacttctt    6000
gcaccaaggt ctctatctgt tcttcaggaa ctccaagaac agactctgcc tccgctaacg    6060
ccaccgcctc ttctgcgcta aaggccaagt cttttctcggt gtactcccgc atagcgcctg    6120
caagtttaag ctgcgagaac ccttttattg tattgcctgc aactgcaaac ctgatatttt     6180
ttggtgtatt taacataaac tccataagtg cgtgcaacaa cggcaagtct aagtcatgat    6240
taatattatc caaacaaact agcgtttcta tctcgttatt cgaggtgctc tgccaaagac    6300
tagatgcaag gtctcgcaag agcgcaggct tgctcacacc ctctctcaca cggctgaatt    6360
ttaccatttc gaaagtttca agctgctcaa taatctctgc gcagatatca aattcactgt    6420
aagaactggc tcttaaagaa agccacactg caggacgtcc ggctgttctg tggcgtagcc    6480
actcgaacgc aagagcaacg gttttcccat atccaggtgg ggctctgtaa aggcatactc    6540
tgggagcggc tccatccgcg atactcaatc ttggccgata tatgcaacta tgaactttgg    6600
cacttactag agtcgtaatt tgatccgctc cgaccttagc gaccgggaaa tcattattta    6660
ttattatttt cattatgcta ttctcgcgcc agctgactgg aaattttcac cataggttac    6720
ggtgttaaat attaaaacta cacttaagtg tagtcggcat gatcggtggt gcaaaatatt    6780
tactagggaa ggtctgaagt aggccgctat ttctggccga cttcggcctt cgccgatttt    6840
gaagacgggc accgggtcaa aatcgaccag atagctcgct catttcggtg ctttcagccg    6900
tcgcgagtag ctcgcggtac ctggcatgct tgcggccagc tcgtgttttt ccagcagacg    6960
acggagcaaa aactacccgt aggtgtagtt ggcgcaagcg tccgattagc tcaggtttaa    7020
gatgtcgaga gtgagagtgg gcggcttaac tttctcagtt aggcataaaa ttacgtctta    7080
aatctcgtag cgactaattt aataaaaatt ggagaattcc atatgcttga gaaacacaga    7140
gttctggatt ccgctccaga gtacgtagat aaaaagaaat atctctggat actatcaact    7200
```

```
ttgtggccgg ctactccgat gatcggaatc tggcttgcaa atgaaactgg ttggggatt    7260 ttttatgggc tggtattgct cgtatggtac ggcgcacttc cattgcttga tgcgatgttt    7320
ggtgaggact ttaataatcc gcctgaagaa gtggtgccga aactagagaa ggagcggtac    7380
tatcgagttt tgacatatct aacagttcct atgcattacg ctgcattaat tgtgtcagca    7440
tggtgggtcg gaactcagcc aatgtcttgg cttgaaattg gtgcgcttgc cttgtcactg    7500
ggtatcgcca acggactagc gctcaataca ggacacgaac tcggtcacaa gaaggagact    7560
tttgatcgtt ggatggccaa aattgtgttg gctgtcgtag ggtacggtca cttctttatt    7620
gagcataata agggtcatca ccgtgatgtc gctacaccga tggatcctgc aacatcccgg    7680
atgggagaaa gcatttataa gttttcaatc cgtgagatcc caggagcatt tattcgtgct    7740
tgggggcttg aggaacaacg ccttcgcgc cgtggccaaa gcgtttggag tttcgataat    7800
gaaatcctcc aaccaatgat catcacagtt attctttacg ccgttctcct tgccttgttt    7860
ggacctaaga tgctggtgtt cctgccgatt caaatggctt tcggttggtg gcagctgacc    7920
agtgcgaact atattgaaca ttacggcttg ctccgtcaaa aaatggagga cggtcgatat    7980
gagcatcaaa agccgcacca ttcttggaat agtaatcaca tcgtctctaa tctagtgctg    8040
ttccaccttc agcggcactc ggatcaccac gcgcatccaa cacgttctta tcagtcactt    8100
cgggattttc ccggcctgcc ggctcttccg acgggttacc ctggtgcatt tttgatggcg    8160
atgattcctc agtggtttag atcagttatg gatcccaagg tagtagattg ggctggtggt    8220
gaccttaata agatccaaat tgatgattcg atgcgagaaa cctatttgaa aaaatttggc    8280
actagtagtg ctggtcatag ttcgagtacc tctgcggtag catcgtagtt atgtgagcac    8340
gcagagcccg gcggtcgata tttacaataa gtgcttcaat tttatgtgcg gcgttgaaag    8400
ctctcacaaa gagtgcactt cgctaaagtg ctgagggttg attgcctctc tgtaattgct    8460
ttgaaggcga cctgctccga tagttacact ctgatgaagt tgtcggagca gcgactaacg    8520
ctgagttaat aggagagtgg gagaatgtca aggtaccagt gtccagattg tcagtatatc    8580
tatgatgaaa ataaggggga gccgcacgaa ggtttccacc cgaacaccag ctggaatgat    8640
atccccaaag attgggcatg cccggactgc gcagttcgag acaaggtgga cttatctttt    8700
ctcgcggatt ctccctcgaa agaaacacag ctaggggtga atagtcagct tgccaactcg    8760
gaaagtggta tttcagatgc tactccaact ggaatggcag ttttggccgc agaattagtg    8820
atcccactta atcaagaaaa taaaaatgag ggctgtgcgg ctaagactga agttcttgat    8880
caggcgagca ccccacaggt tgtaagaaaa tcttccacaa ggaagaagat gagaaataaa    8940
taacgcaaat ttgccgcaac gcaaaataac aatttgacat ggtgatgagt atggctagct    9000
ataaatgccc ggattgtaat tatgtttatg atgagagtgc gggtaatgtg catgaggggt    9060
tttctccagg tacgccttgg caccttattc ctgaggattg gtgctgcccc gattgcgccg    9120
ttcgagacaa gcttgacttc atgttaattg agagcggcgt aggtgaaaag ggcgtcacct    9180
caacccatac ttcgccaaat ttatccgagg ttagtggcac aagtttaact gctgaagcag    9240
tggttgcgcc gacaagctta gagaaattgc ctagtgccga cgttaaaggc caagatctat    9300
ataaaactca acctccaagg tctgatgccc aaggcgggaa agcatacttg aagtggatat    9360
gtattacttg tggccatata tatgatgagg cgttgggcga tgaggccgag ggttttactc    9420
caggtactcg ctttgaggat attcctgatg actggtgctg tccggattgc ggggctacga    9480
aagaagacta tgtgctctac gaggaaaagt gaagattaaa acttcaagtc attctaggta    9540
```

```
attcaggaca aaataaaaat gaccatacca attagcctag ccaagttaaa ctctagtgcc    9600
gatacccatt cagcgcttgt cgacctgtaa cgacaacaaa acgagggtag cacaatgagt    9660
ttttctaatt ataaagtaat cgcgatgccg gtgttggttg ctaattttgt tttggggcg     9720
gccactgcat gggcgaatga aaattatccg gcgaaatctg ctggctataa tcagggtgac    9780
tgggtcgcta gcttcaattt ttctaaggtc tatgtgggtg aggagcttgg cgatctaaat    9840
gttggagggg gggctttgcc aaatgctgat gtaagtattg gtaatgatac aacacttacg    9900
tttgatatcg cctattttgt tagctcaaat atagcggtgg atttttttgt tggggtgcca    9960
gctagggcta aatttcaagg tgagaaatca atctcctcgc tgggaagagt cagtgaagtt   10020
gattacggcc ctgcaattct ttcgcttcaa tatcattacg atagctttga gcgactttat   10080
ccatatgttg gggttggtgt tggtcgggtg ctattttttg ataaaaccga cggtgctttg   10140
agttcgtttg atattaagga taaatgggcg cctgcttttc aggttggcct tagatatgac   10200
cttggtaact catggatgct aaattcagat gtgcgttata ttcctttcaa aacgacgtc    10260
acaggtactc ttggcccggt tcctgtttct actaaaattg aggttgatcc tttcattctc   10320
agtcttggtg cgtcatatgt tttctaagta atcaggtctg tcactgtcgc aggtcgacct   10380
gcagccaagc ttctgttttg gcggatgaga aagattttc agcctgatac agattaaatc    10440
agaacgcaga agcggtctga taaaacagaa tttgcctggc ggcagtagcg cggtggtccc   10500
acctgacccc atgccgaact cagaagtgaa acgccgtagc gccgatggta gtgtggggtc   10560
tccccatgcg agagtaggga actgccaggc atcaaataaa acgaaaggct cagtcgaaag   10620
actgggcctt tcgttttatc tgttgtttgt cggtgaacgc tctcctgagt aggacaaatc   10680
cgccgggagc ggatttgaac gttgcgaagc aacggcccgg agggtggcgg caggacgcc    10740
cgccataaac tgccaggcat caaattaagc agaaggccat cctgacggat ggccttttg    10800
cgtttctaca aactcttttg tttatttttc taaatacatt caaatatgta tccgctcatg   10860
agacaataac cctgataaat gcttcaataa tgcagcctga aaggcaggcc gggccgtggt   10920
ggccacggcc tctaggccag atccagcggc atctgggtta gtcgagcgcg gccgcttcc    10980
catgtctcac cagggcgagc ctgtttcgcg atctcagcat ctgaaatctt cccggccttg   11040
cgcttcgctg ggccttacc caccgccttg gcgggcttct tcggtccaaa actgaacaac    11100
agatgtgtga ccttgcgccc ggtctttcgc tgcgcccact ccacctgtag cgggctgtgc   11160
tcgttgatct gcgtcacggc tggatcaagc actcgcaact tgaagtcctt gatcgaggga   11220
taccggcctt ccagttgaaa ccactttcgc agctggtcaa tttctatttc gcgctggccg   11280
atgctgtccc attgcatgag cagctcgtaa agcctgatcg cgtgggtgct gtccatcttg   11340
gccacgtcag ccaaggcgta tttggtgaac tgtttggtga gttccgtcag gtacggcagc   11400
atgtctttgg tgaacctgag ttctacacgg ccctcacccct cccggtagat gattgtttgc   11460
acccagccgg taatcatcac actcggtctt ttccccttgc cattgggctc ttgggttaac   11520
cggacttccc gccgtttcag gcgcagggcc gcttctttga gctggttgta ggaagattcg   11580
atagggacac ccgccatcgt cgctatgtcc tccgccgtca ctgaatacat cacttcatcg   11640
gtgacaggct cgctcctctt cacctggcta atacaggcca gaacgatccg ctgttcctga   11700
acactgaggc gatacgcggc ctcgaccagg gcattgcttt tgtaaaccat tggggtgag    11760
gccacgttcg acattccttg tgtataaggg gacactgtat ctgcgtccca caatacaaca   11820
aatccgtccc tttacaacaa caaatccgtc ccttcttaac aacaaatccg tcccttaatg   11880
gcaacaaatc cgtcccttt taaactctac aggccacgga ttacgtggcc tgtagacgtc   11940
```

```
ctaaaaggtt taaaagggaa aaggaagaaa agggtggaaa cgcaaaaaac gcaccactac   12000
gtggccccgt tggggccgca tttgtgcccc tgaagggcg ggggaggcgt ctgggcaatc    12060
cccgttttac cagtcccta tcgccgcctg agagggcgca ggaagcgagt aatcagggta    12120
tcgaggcgga ttcaccttg gcgtccaacc agcggcacca gcggcgcctg agaggcgaat    12180
tgacataagc ctgttcggtt cgtaaactgt aatgcaagta gcgtatgcgc tcacgcaact   12240
ggtccagaac cttgaccgaa cgcagcggtg gtaacggcgc agtggcggtt ttcatggctt    12300
gttatgactg ttttttgta cagtctatgc ctcgggcatc caatcgat                 12348
```